United States Patent
Rich et al.

(10) Patent No.: US 9,731,032 B2
(45) Date of Patent: Aug. 15, 2017

(54) APTAMERS FOR TUMOR INITIATING CELLS

(71) Applicant: THE CLEVELAND CLINIC FOUNDATION, Cleveland, OH (US)

(72) Inventors: Jeremy N. Rich, Cleveland, OH (US); Youngmi Kim, Cleveland, OH (US); Anita B. Hjelmeland, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/763,283

(22) PCT Filed: Feb. 4, 2014

(86) PCT No.: PCT/US2014/014608
§ 371 (c)(1),
(2) Date: Jul. 24, 2015

(87) PCT Pub. No.: WO2014/121256
PCT Pub. Date: Aug. 7, 2014

(65) Prior Publication Data
US 2015/0366996 A1 Dec. 24, 2015
US 2017/0165376 A9 Jun. 15, 2017

Related U.S. Application Data

(60) Provisional application No. 61/760,376, filed on Feb. 4, 2013.

(51) Int. Cl.
| | |
|---|---|
| *C12N 15/115* | (2010.01) |
| *A61K 45/00* | (2006.01) |
| *A61K 47/48* | (2006.01) |
| *A61K 49/00* | (2006.01) |
| *A61K 47/10* | (2017.01) |
| *G01N 33/574* | (2006.01) |

(52) U.S. Cl.
CPC ........ *A61K 47/48907* (2013.01); *A61K 47/10* (2013.01); *A61K 47/48092* (2013.01); *A61K 47/48915* (2013.01); *A61K 49/0002* (2013.01); *C12N 15/115* (2013.01); *G01N 33/57407* (2013.01); *C12N 2310/16* (2013.01); *C12N 2310/3517* (2013.01); *C12N 2320/30* (2013.01)

(58) Field of Classification Search
CPC .............. A61K 45/00; A61K 47/48092; A61K 47/481; A61K 2121/00; C12N 15/115; C12N 2310/16; C12N 2310/3517; C12N 2320/30; G01N 33/57407
USPC ....................... 424/1.73; 436/56, 57; 514/44; 536/23.1, 25.32
See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 2012/0141382 A1 | 6/2012 | Shi et al. |

OTHER PUBLICATIONS

Weng et al, Microfluid Nanofluid 14:753-765, 2013; available online Nov. 21, 2012.*
Shigdar et al, Cancer Sci. 102:991-998, 2011; available online Mar. 14, 2011.*
Broadley et al, Stem Cells 29:452-461, 2011.*
Subramanian et al, Molecular Vision 18:2783-2795, 2012; available Nov. 22, 2012.*
Bagalkot et al, Angew. Chem. Int. Ed. 45:8149-8152, 2006.*
Anido, Judit, et al. "TGF-β receptor inhibitors target the CD44 high/Id1 high glioma-initiating cell population in human glioblastoma." Cancer cell 18.6 (2010): 655-668.
Bao, Shideng, et al. "Targeting cancer stem cells through L1CAM suppresses glioma growth." Cancer research 68.15 (2008): 6043-6048.
Chen, Xue-Chai, et al. "Quantum dot-labeled aptamer nanoprobes specifically targeting glioma cells." Nanotechnology 19.23 (2008): 235105.
Donovan, Michael J., et al. "Aptamer—drug conjugation for targeted tumor cell therapy." Therapeutic Oligonucleotides. Humana Press, 2011. 141-152.
Gao, Huile, et al. "Whole-cell SELEX aptamer-functionalised poly (ethyleneglycol)-poly (ε-caprolactone) nanoparticles for enhanced targeted glioblastoma therapy." Biomaterials 33.26 (2012): 6264-6272.
Srinivasan et al., BACPP35-B17.z Pristionchus pacificus BAC ends *Pristionchus pacificus* genomic, genomic survey sequence, GenBank, May 20 2002, 1 page.
Goidts, V., et al. "RNAi screening in glioma stem-like cells identifies PFKFB4 as a key molecule important for cancer cell survival." Oncogene 31.27 (2012): 3235-3243.
Hemmati, Houman D., et al. "Cancerous stem cells can arise from pediatric brain tumors." Proceedings of the National Academy of Sciences 100.25 (2003): 15178-15183.

(Continued)

*Primary Examiner* — Kevin Hill
(74) *Attorney, Agent, or Firm* — Tarolli, Sundheim, Covell & Tummino LLP

(57) ABSTRACT

Aptamers consisting of a single stranded nucleic acids having 100 nucleotides or less that specifically binds to tumor initiating cancer cells are described. The aptamers can be identified by screening a large pool of randomly generated aptamers to obtain a discrete set of aptamers that specifically bind to tumor initiating cancer cells, such as those found in brain cancer or glioblastoma. The aptamers can also be linked or complexed with anticancer agents or imaging agents for use in therapy or diagnosis.

29 Claims, 9 Drawing Sheets

(56) References Cited

OTHER PUBLICATIONS

Huang, Yu-Fen, Huan-Tsung Chang, and Weihong Tan. "Cancer cell targeting using multiple aptamers conjugated on nanorods." Analytical chemistry 80.3 (2008): 567-572.
Ko, Hae Young, et al. "A nucleolin-targeted multimodal nanoparticle imaging probe for tracking cancer cells using an aptamer." Journal of Nuclear Medicine 51.1 (2010): 98-105.
Inowa, Toshihiko, et al. "GADD45 ? Determines Chemoresistance and Invasive Growth of Side Population Cells of Human Embryonic Carcinoma." Stem cells international 2010 (2010).
Jin, Xun, et al. "EGFR-AKT-Smad signaling promotes formation of glioma stem-like cells and tumor angiogenesis by ID3-driven cytokine induction." Cancer research 71.22 (2011): 7125-7134.
Kang, Dezhi, et al. "Selection of DNA aptamers against glioblastoma cells with high affinity and specificity." (2012): e42731.
Kim, Youngmi, et al. "Aptamer Identification of Brain Tumor-Initiating Cells." Cancer research 73.15 (2013): 4923-4936.
Kim, Youngmi, et al. "Platelet-derived growth factor receptors differentially inform intertumoral and intratumoral heterogeneity." Genes & development 26.11 (2012): 1247-1262.
Lathia, Justin D., et al. "Integrin alpha 6 regulates glioblastoma stem cells." Cell stem cell 6.5 (2010): 421-432.
Lew, Qiao Jing, et al. "Identification of HEXIM1 as a positive regulator of p53." Journal of Biological Chemistry 287.43 (2012): 36443-36454.
Pu, Ying, et al. "Using aptamers to visualize and capture cancer cells." Analytical and bioanalytical chemistry 397.8 (2010): 3225-3233.
Salmaggi, Andrea, et al. "Glioblastoma-derived tumorospheres identify a population of tumor stem-like cells with angiogenic potential and enhanced multidrug resistance phenotype." Glia 54.8 (2006): 850-860.
Sefah, Kwame, et al. "Development of DNA aptamers using Cell-SELEX." Nature protocols 5.6 (2010): 1169-1185.
Sefah, Kwame, et al. "Cell-based selection provides novel molecular probes for cancer stem cells." International Journal of Cancer 132.11 (2013): 2578-2588.
Shigdar, Sarah, et al. "RNA aptamers targeting cancer stem cell marker CD133." Cancer letters 330.1 (2013): 84-95.
Singh, Sheila K., et al. "Cancer stem cells in nervous system tumors." Oncogene 23.43 (2004): 7267-7273.
Son, Myung Jin, et al. "SSEA-1 is an enrichment marker for tumor-initiating cells in human glioblastoma." Cell stem cell 4.5 (2009): 440-452.
Tan, Weihong, et al. "Molecular aptamers for drug delivery." Trends in biotechnology 29.12 (2011): 634-640.
Verhaak, Roel GW, et al. "Integrated genomic analysis identifies clinically relevant subtypes of glioblastoma characterized by abnormalities in PDGFRA, IDH1, EGFR, and NF1." Cancer cell 17.1 (2010): 98-110.
Yang, Liu, et al. "Aptamer-conjugated nanomaterials and their applications." Advanced drug delivery reviews 63.14 (2011): 1361-1370.
Ye, Mao, et al. "Generating aptamers by cell-SELEX for applications in molecular medicine." International journal of molecular sciences 13.3 (2012): 3341-3353.
Ying, Jianming, et al. "The stress-responsive gene GADD45G is a functional tumor suppressor, with its response to environmental stresses frequently disrupted epigenetically in multiple tumors." Clinical Cancer Research 11.18 (2005): 6442-6449.
Zhang, Jing, et al. "A dialog between glioma and microglia that promotes tumor invasiveness through the CCL2/CCR2/interleukin-6 axis." Carcinogenesis (2011): bgr289.
PCT International Search Report and Written Opinion for PCT/US2014/014608, mailed Feb. 4, 2014, pp. 1-16.

\* cited by examiner

SEQUENCE LISTING

<160> NUMBER OF SEQ ID NOS: 15

<210> SEQ ID NO 1
<211> LENGTH: 29
<212> TYPE: DNA
<213> ORGANISM: Artificial Sequence
<220> FEATURE:
<223> OTHER INFORMATION: APTAMER 1

<400> SEQUENCE: 1
gacgagctaa gaacctttag gagtggaaa                                              29

<210> SEQ ID NO 2
<211> LENGTH: 29
<212> TYPE: DNA
<213> ORGANISM: Artificial Sequence
<220> FEATURE:
<223> OTHER INFORMATION: APTAMER 2

<400> SEQUENCE: 2
ccgtagctac gacggaggaa actatgtta                                              29

<210> SEQ ID NO 3
<211> LENGTH: 29
<212> TYPE: DNA
<213> ORGANISM: Artificial Sequence
<220> FEATURE:
<223> OTHER INFORMATION: APTAMER 3

<400> SEQUENCE: 3
aaagctcctt ggaatagtct aataccgga                                              29

<210> SEQ ID NO 4
<211> LENGTH: 29
<212> TYPE: DNA
<213> ORGANISM: Artificial Sequence
<220> FEATURE:
<223> OTHER INFORMATION: APTAMER 4

<400> SEQUENCE: 4
tgtgtataaa ggggcggtga aaagcgaat                                              29

<210> SEQ ID NO 5
<211> LENGTH: 29
<212> TYPE: DNA
<213> ORGANISM: Artificial Sequence
<220> FEATURE:
<223> OTHER INFORMATION: APTAMER 5

<400> SEQUENCE: 5
agaactggcc ttactacgaa aagtccttg                                              29

<210> SEQ ID NO 6
<211> LENGTH: 30
<212> TYPE: DNA
<213> ORGANISM: Artificial Sequence
<220> FEATURE:
<223> OTHER INFORMATION: APTAMER 6

<400> SEQUENCE: 6
ccaaaagaat aagacaacta ggtaagcttt                                             30

<210> SEQ ID NO 7
<211> LENGTH: 30
<212> TYPE: DNA
<213> ORGANISM: Artificial Sequence

```
<220> FEATURE:
<223> OTHER INFORMATION: APTAMER 7

<400> SEQUENCE: 7
actttgggcc gtaacgatta gtgccctct                                            30

<210> SEQ ID NO 8
<211> LENGTH: 30
<212> TYPE: DNA
<213> ORGANISM: Artificial Sequence
<220> FEATURE:
<223> OTHER INFORMATION: APTAMER 8

<400> SEQUENCE: 8
aaaagctcct tggaatagtc taataccgga                                           30

<210> SEQ ID NO 9
<211> LENGTH: 30
<212> TYPE: DNA
<213> ORGANISM: Artificial Sequence
<220> FEATURE:
<223> OTHER INFORMATION: APTAMER 9

<400> SEQUENCE: 9
agaactggcc ttactacgaa aagtcctttgg                                          30

<210> SEQ ID NO 10
<211> LENGTH: 86
<212> TYPE: DNA
<213> ORGANISM: Artificial Sequence
<220> FEATURE:
<223> OTHER INFORMATION: COMPLETE APTAMER 1

<400> SEQUENCE: 10
atccacgagt gacgcagcac agagtggaag acgagctaag aacctttagg agtggaaaag         60
atagctcatg gacacggtgg cttagt                                              86

<210> SEQ ID NO 11
<211> LENGTH: 87
<212> TYPE: DNA
<213> ORGANISM: Artificial Sequence
<220> FEATURE:
<223> OTHER INFORMATION: COMPLETE APTAMER 2

<400> SEQUENCE: 11
atccacgagt gacgcagcat gtttaggaaa ccgtagctac gacggaggaa actatgttaa         60
acatccccat ggacacggtg gcttagt                                             87

<210> SEQ ID NO 12
<211> LENGTH: 87
<212> TYPE: DNA
<213> ORGANISM: Artificial Sequence
<220> FEATURE:
<223> OTHER INFORMATION: COMPLETE APTAMER 3

<400> SEQUENCE: 12
atccacgagt gacgcagcac gagcaacaca aaagctcctt ggaatagtct aataccggag         60
cgagaaagct ggacacggtg gcttagt                                             87

<210> SEQ ID NO 13
<211> LENGTH: 87
<212> TYPE: DNA
<213> ORGANISM: Artificial Sequence
<220> FEATURE:
```

```
<223> OTHER INFORMATION: COMPLETE APTAMER 4

<400> SEQUENCE: 13
atccacgagt gacgcagcac agtgatcagt tgtgtataaa ggggcggtga aaagcgaatt    60
ccagtcgact ggacacggtg gcttagt                                        87

<210> SEQ ID NO 14
<211> LENGTH: 87
<212> TYPE: DNA
<213> ORGANISM: Artificial Sequence
<220> FEATURE:
<223> OTHER INFORMATION: COMPLETE APTAMER 5

<400> SEQUENCE: 14
atccacgagt gacgcagcac cgagaggaga gaactggcct tactacgaaa agtccttggt    60
tgccaggggt ggacacggtg gcttagt                                        87

<210> SEQ ID NO 15
<211> LENGTH: 86
<212> TYPE: DNA
<213> ORGANISM: Artificial Sequence
<220> FEATURE:
<223> OTHER INFORMATION: COMPLETE APTAMER 6

<400> SEQUENCE: 15
tccacgagtg acgcagcacg tgagtaaacc aaaagaataa gacaactagg taagctttgc    60
aagggtagtg gacacggtgg cttagt                                        86
```

APTAMERS FOR TUMOR INITIATING CELLS

CONTINUING APPLICATION DATA

This application claims the benefit of U.S. Provisional Application Ser. No. 61/760,376, filed Feb. 4, 2013, which is incorporated by reference herein.

GOVERNMENT FUNDING

This work was supported, at least in part, by grant numbers CA129958, CA116659, CA154130, CA151522, CA137443, NS063971, CA128269, CA101954, and CA116257 from the Department of Health and Human Services, National Institutes of Health. The United States government has certain rights in this invention.

SEQUENCE LISTING

The instant application contains a Sequence Listing which has been submitted electronically in ASCII format and is hereby incorporated by reference in its entirety. Said ASCII copy, created on Feb. 3, 2014, is named CCF-022018WOORD_SEQLIST.txt and is 3,482 bytes in size.

BACKGROUND

Cancers invoke molecular programs expressed during development and wound responses to promote the initiation and maintenance of complex neoplastic tissue systems that include not only transformed cells but also supportive vasculature, immune components, stroma, and extracellular matrix. Standard human cancer models based on established cell lines are subjected to passage under conditions that select for rapid proliferation and survival through mechanisms often distinct from the original tumor. While proliferation and resistance to apoptosis are hallmarks of cancer, other aspects of cancer—invasion of normal tissues, metastasis, resistance to cytotoxic insults and vascular recruitment—critically contribute to the lethality of cancer. An increasing number of cancers have been shown to display cellular hierarchies with a subset of the neoplastic compartment activating molecular mechanisms and cellular phenotypes similar—but not identical—to embryonic or tissue-specific stem cells. These cancer stem cells, also called tumor initiating cells (TICs) or tumor propagating cells, are functionally defined through assays of self-renewal and tumor propagation. It has been shown that TICs are relatively resistant to conventional cancer therapies (radiotherapy and chemotherapy) and promote tumor growth through angiogenesis. Bao et al., Cancer research, 66:7843-8 (2006); Cheng et al., Biochemical and biophysical research communications, 406:643-8 (2011). The TIC hypothesis has been questioned because of potential plasticity of the cellular hierarchy and difficulties with TIC identification but these challenges are products of the inventors' attempts to simplify complex systems with limited technical resources. Based on this background, creating agents that prospectively identify TICs may not only permit the interrogation of the cellular hierarchy in cancers but also serve as a platform for the development of novel targeted therapies and imaging reagents.

Glioblastoma (GBM) is the most prevalent and lethal primary brain tumor and ranks among the most lethal of all cancers. Through the work of many groups the presence of a cellular hierarchy has been supported in not only GBM but also other central nervous system cancers. Singh et al., Oncogene, 23:7267-73 (2004); Hemmati et al., PNAS, 100: 15178-83 (2003). The characterization of TICs is based on paradigms developed from embryonic and tissue-specific stem cells but TICs are distinct from these normal cells so the immunophenotypes are likely non-overlapping in part. Several surface TIC markers have shown promise in GBM, including CD133 (Prominin-1) (Salmaggi et al., Glia, 54:850-60 (2006)), CD15/Lewis X-antigen/stage specific embryonic antigen-1 (SSEA-1) (Son et al., Cell stem cell, 4:440-52 (2009)), CD44 (Anido et al., Cancer cell., 18:655-68 (2010)), L1CAM (Bao et al., Cancer research, 68:6043-8 (2008)), integrin α6 (Lathia et al., Cell stem cell, 6:421-32 (2010)), epidermal growth factor receptor (EGFR) (Jin et al., Cancer research, 71:7125-34 (2011)), and platelet derived growth factor receptor β (PDGFRβ) (Kim et al., Genes & development, 26:1247-62 (2012)). Functional assays, including Aldefluor and side population, have been less reliable in GBM but useful in other cancer types. Broadley et al., Stem cells, 29:452-61 (2011).

Neurosphere formation has been used to enrich for TICs but this method prevents the prospective separation of tumorigenic and non-tumorigenic cells that define a cellular hierarchy. While these markers have been useful in some studies to prospectively enrich or deplete TICs, many of these have been limited by a shared antigen with normal neural progenitors. Several groups have taken other approaches to identify TIC targets. RNA interference screens have identified key transcription factors, kinases, phosphatases, or ubiquitin-modifying enzymes. Goidts et al., Oncogene, 31:3235-43 (2012). One group reported a TIC screen in prostate cancer stem cells (Sefah et al., Int. J. cancer, 132(11):2578-88 (2012)), and other identified CD133 binding aptamers (Shigdar et al., Cancer letters, 330(1):84-95 (2013)). However, a large screen to identify novel TIC enrichment reagents in GBM has not previously been developed.

SUMMARY

Glioblastomas (GBM) display cellular hierarchies with self-renewing tumor initiating cells (TICs), also known as cancer stem cells, at the apex. Although the TIC hypothesis remains controversial and the functional assays to define the TIC phenotype are evolving, it has been demonstrated that TICs may contribute to therapeutic resistance, tumor spread, and angiogenesis. The identification of TICs has been informed by the use of markers characterized in normal stem cells but this approach has an inherent limitation to selectively identify TICs. To develop reagents that enrich for TICs but not matched non-TICs or tissue-specific stem cells, the inventors adopted Cell-Systematic Evolution of Ligands by Exponential Enrichment (Cell-SELEX) to identify GBM TIC-specific nucleic acid probes—aptamers—that specifically bind TICs. In the work described herein, using Cell-SELEX with positive selection for TICs and negative selection for non-TICs and human neural progenitor cells (NPCs), TIC aptamers were identified that specifically bind to TICs with excellent $K_d$S. These aptamers select GBM cells that self-renew, proliferate, and initiate tumors. As aptamers can be modified to deliver payloads, aptamers represent novel agents that could selectively target or facilitate the imaging of TICs.

In one aspect, the invention provides an aptamer consisting of a single stranded nucleic acid having 100 nucleotides or less that specifically binds to tumor initiating cancer cells. In some embodiments, the tumor initiating cancer cells are brain cancer cells, while in other embodiments the tumor initiating cancer cells are glioblastoma cells. In further embodiments, the nucleic acid is DNA. In further embodiments, the aptamer includes a sequence selected from the group consisting of SEQ ID NOS. 1-9, or a homolog or analog thereof.

Another aspect of the invention provides a method of imaging tumor initiating cancer cells in a subject that includes administering an effective amount of an aptamer consisting of a single stranded nucleic acid having 100 nucleotides or less that specifically binds to tumor initiating cancer cells, the aptamer being complexed or linked to an imaging agent, to the subject and detecting the aptamers with an imaging apparatus. In some embodiments, the aptamer specifically binds to tumor initiating brain cancer cells, while in other embodiments the aptamer specifically binds to tumor initiating glioblastoma cells. The method can be used to image tumor initiating cancer cells either in vivo or in vitro. The aptamer comprises a sequence selected from the group consisting of SEQ ID NOS. 1-9, or a homolog or analog thereof.

Another aspect of the invention provides a method of treating cancer in a subject, comprising administering an effective amount of an aptamer consisting of a single stranded nucleic acid having 100 nucleotides or less that specifically binds to cancer cells, the aptamer being complexed or linked to an anticancer agent, to the subject. In some embodiments, the cancer cell is a tumor initiating cell and the aptamer specifically binds to tumor initiating cells. In other embodiments, the cancer is brain cancer and the aptamer specifically binds to brain cancer cells. In yet further embodiments, the cancer is glioblastoma and the aptamer specifically binds to glioblastoma cells. In further embodiments, the aptamer includes a sequence selected from the group consisting of SEQ ID NOS. 1-9, or a homolog or analog thereof.

BRIEF DESCRIPTION OF THE FIGURES

FIG. 1(D) discloses SEQ ID NOS 1-9, respectively, in order of appearance.

(C6)-loaded nanoparticles in the rat brain. Scale bar=1 mm. (c). Fluorescence microscopy image of C6 loaded nanoparticles delivered in 338 ul PBS in the pig brain. Scale bar=1 cm. (d). Inhibitory effects of DI on BCSC proliferation (IC50), self-renewal (neurosphere (NS) formation) and decrease of CD133-+ cells, c. Kaplan-Meier survival curves for tumor-bearing rats with indicated treatments: lines from right to left are brain-penetrating DI NPs; standard DI NPs; free DI; blank NPs; no treatment.

Figure 9:
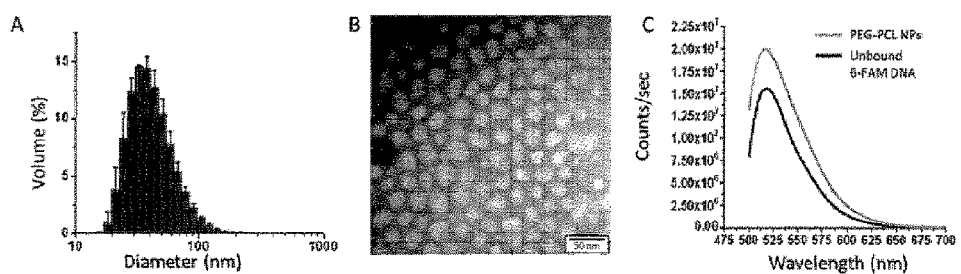

FIG. 9 provides graphs and images showing Characterization of PEG-PCL nanoparticles conjugated with TIC-specific aptamers. (a) Following synthesis, PEG-PCL NPs were evaluated by DLS for hydrodynamic radius, Particle size distribution is displayed based on particle volume with error bars for each size bin is shown. (b) To confirm DLS measurements, NPs were visualized by TEM after negative staining with 2% PTA. Scale bar is 50 nm. (c) After coupling to TIC-specific aptamers with EDC chemistry, PEG-PCL NPs were analyzed via fluorometer for the presence of 6-FAM bound to the aptamer strand. For comparison, unbound 6-FAM labeled DNA is shown. Samples were excited at 494 nm and emission collected from 500 to 700 nm.

Figure 10:
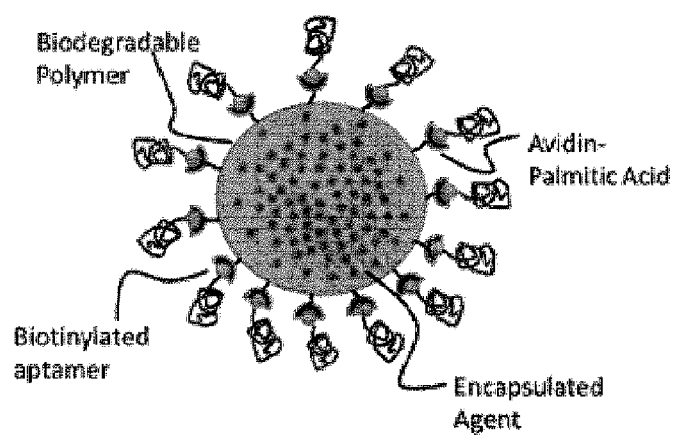

FIG. 10 provides a schematic of aptamer-conjugated nanoparticles

DETAILED DESCRIPTION

Unless otherwise defined, all technical and scientific terms used herein have the same meaning as commonly understood by one of ordinary skill in the art to which this application pertains. Although methods and materials similar or equivalent to those described herein can be used in the practice or testing of the exemplary embodiments, suitable methods and materials are described below. In case of conflict, the present specification, including definitions, will control. In addition, the materials, methods, and examples are illustrative only and not intended to be limiting.

The terminology as set forth herein is for description of the embodiments only and should not be construed as limiting the application as a whole. Unless otherwise specified, "a," "an," "the," and "at least one" are used interchangeably. Furthermore, as used in the description of the application and the appended claims, the singular forms "a", "an", and "the" are inclusive of their plural forms, unless contraindicated by the context surrounding such. Furthermore, the recitation of numerical ranges by endpoints includes all of the numbers subsumed within that range (e.g., 1 to 5 includes 1, 1.5, 2, 2.75, 3, 3.80, 4, 5, etc.).

The term "isolated" means that the material is removed from its original environment (e.g., the natural environment if it is naturally occurring) or is synthetically derived. For example, a naturally-occurring nucleic acid present in a living animal is not isolated, but the same nucleic acid, separated from some or all of the coexisting materials in the natural system, is isolated. Such a nucleic acid could be part of a composition, and still be isolated in the composition, and not be a part of its natural environment.

The term "nucleic acid," as used herein, refers to DNA (deoxyribonucleic acid) and RNA (ribonucleic acid), which are polymeric macromolecules made from monomers known as nucleotides. Each nucleotide has three components: a 5-carbon sugar, a phosphate group, and a purine or pyrimidine nitrogenous base. If the sugar is deoxyribose, the polymer is DNA. If the sugar is ribose, the polymer is RNA. The bases found in DNA and RNA include adenine (A), cytosine (C), and guanine (G), while thymine (T) is only found in DNA and uracil (U) is only found in RNA. Unless otherwise indicated, the nucleic acids described herein are single stranded and can also include modified nucleotides.

As used herein, the terms "treatment," "treating," or "treat" refer to any treatment of brain cancer in a subject including, but not limited to, inhibiting disease development, arresting development of clinical symptoms associated with the disease, and/or relieving the symptoms associated with the disease. However, the terms "treating" and "ameliorating" do not necessarily meant to indicate a reversal or cessation of the disease process underlying the asthma or inflammation afflicting the subject being treated. Such terms indicate that the deleterious signs and/or symptoms associated with the condition being treated are lessened or reduced, or the rate of progression is reduced, compared to that which would occur in the absence of treatment. A change in a disease sign or symptom can be assessed at the level of the subject (e.g., the function or condition of the subject is assessed), or at a tissue or cellular level.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

As used herein, the term "effective amount" refers to an amount of an aptamer, particular an aptamer complexed or linked to an anticancer agent or imaging agent, that is sufficient to provide a desired effect. For example, a "diagnostically effective amount" enables the imaging of the contrast agent in cells, tissues, or organisms using imaging equipment, while a "therapeutically effective amount" provides an amount that is effective to reduce or arrest a disease or disorder such as abnormal cell growth in a subject. The result can be a reduction and/or alleviation of the signs, symptoms, or causes of a disease or disorder, or any other desired alteration of a biological system. The effectiveness of treatment may be measured by evaluating a reduction in tumor load or decrease in tumor growth in a subject in response to the administration of aptamers. The reduction in tumor load may be represent a direct decrease in mass, or it may be measured in terms of tumor growth delay, which is calculated by subtracting the average time for control tumors to grow over to a certain volume from the time required for treated tumors to grow to the same volume. An effective amount in any individual case may be determined by one of ordinary skill in the art using routine experimentation.

The present invention provides single stranded nucleic acid aptamers that specifically bind to tumor initiating cancer cells. Most cancers display cellular hierarchies that are based on tumor initiating cells (TICs), and many of these TICs share molecular targets such that an aptamer developed against one type of cancer may often be useful against other types of cancer as well. The aptamers can be used for imaging tumor initiating cancer cells, and for treating cancers that include tumor initiating cells, such as brain cancer and glioblastoma, particularly when the aptamers are linked or complexed to anticancer or imaging agents.

Aptamers

An aptamer is a nucleic acid that binds with high specificity and affinity to a particular target molecule or cell structure, through interactions other than Watson-Crick base pairing. Aptamer functioning is unrelated to the nucleotide sequence itself, but rather is based on the secondary/tertiary structure formed, and are therefore best considered as non-coding sequences. Aptamers of the present invention may be single stranded RNA, DNA, a modified nucleic acid, or a mixture thereof. The aptamers can also be in a linear or circular form. Accordingly, in some embodiments, the aptamers are single stranded DNA, while in other embodiments they are single stranded RNA.

The length of the aptamer of the present invention is not particularly limited, and can usually be about 10 to about 200 nucleotides, and can be, for example, about 100 nucleotides or less, about 50 nucleotides or less, about 40 nucleotides or less, or about 35 nucleotides or less. When the total number of nucleotides present in the aptamer is smaller, chemical synthesis and mass-production will be easier and less costly. In addition, in almost all known cases, the various structural motifs that are involved in the non-Watson-Crick type of interactions involved in aptamer binding, such as hairpin loops, symmetric and asymmetric bulges, and pseudoknots, can be formed in nucleic acid sequences of 30 nucleotides or less.

The aptamers of the invention are capable of specifically binding to brain cancer cells. Specificity is conferred using the methods of identifying aptamers described herein, such as use of the SELEX procedure. Specific binding refers to binding which discriminates between the selected target and other potential targets, and binds with substantial affinity to the selected target. Substantial affinity represents an aptamer having a binding dissociation constant of at least about $10^{-8}$ mol/m$^3$, but in other embodiments, the aptamers can have a binding dissociation constant of at least about $10^{-9}$ mol/m$^3$, about $10^{-10}$ mol/m$^3$, about $10^{-11}$ mol/m$^3$, or at least about $10^{-12}$ mol/m$^3$.

It is preferable than an aptamer that is intended for use as a therapeutic or diagnostic agent be inexpensive to synthesize, safe and relatively stable in vivo. Wild-type RNA and DNA aptamers are not as stable as would be preferred because of their susceptibility to degradation by nucleases. Resistance to nuclease degradation can be greatly increased by the incorporation of modifying groups at the 2'-position. Accordingly, in some embodiments, the aptamers include a modifying group at the 2'-position of one or more nucleotides present in the aptamer. Aptamers including any of the modifying groups described herein are structural analogs of the original aptamer, and are referred to herein as analogs.

Examples of modifications at the 2'-position of pyrimidine or purine nucleotides, which normally is a hydroxyl group, include a nucleotide substituted by a hydrogen atom (i.e., a 2-deoxy nucleotide), a fluorine atom or an —O-alkyl group (e.g., —O-Me group), an —O-acyl group (e.g., —O—CHO group), or an amino group (e.g., —NH$_2$ group). The aptamer of the present invention can also be the modified nucleotide wherein at least one kind (e.g., 1, 2, 3 or 4 kinds) of nucleotide comprises a hydroxyl group, or the above-described modification at the 2'-position, for example, at least two kinds (e.g., 2, 3 or 4 kinds) of groups selected from the group consisting of a hydrogen atom, a fluorine atom, a hydroxyl group and a —O-Me group, at the 2' position of ribose. For methods of making nucleic acids suitable for aptamer screening including modification at the 2'-position, see for example U.S. Pat. No. 8,105,813, entitled "Materials and Methods for the Generation of Fully 2'-Modified Containing Nucleic Acid Transcripts," the disclosure of which is incorporated by reference herein.

Modifications include, but are not limited to, 2'-position sugar modifications. Examples of other modifications of nucleotides include 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, and unusual base-pairing combinations such as the isobases isocytidine and isoguanosine. Modifications can also include 3' and 5' modifications such as capping, e.g., addition of a 3'-3'-dT cap to increase exonuclease resistance (see, e.g., U.S. Pat. Nos. 5,674,685; 5,668,264; 6,207,816; and 6,229,002, each of which is incorporated by reference herein).

An aptamer binds to the target substance in a wide variety of binding modes, such as ionic bonds based on the negative charge of the phosphate group, hydrophobic bonds and hydrogen bonds based on ribose, and hydrogen bonds and stacking interaction based on nucleic acid bases. In particular, ionic bonds based on the negative charge of the phosphate group, which are present in the same number as the number of constituent nucleotides, are strong, and bind to lysine and arginine being present on the surface of the positive charge of protein. For this reason, nucleic acid bases not involved in the direct binding to the target substance can be substituted. In particular, because the region of stem structure has already formed base pairs and faces the inside of the double helical structure, nucleic acid bases are unlikely to bind directly to the target substance. Therefore, even when a base pair is substituted with another base pair, the activity of the aptamer often does not decrease. In structures wherein no base pairs are formed, such as loop structures, provided that the nucleic acid base is not involved in the direct binding to the target molecule, base substitution is possible. Regarding modifications of the 2'-position of ribose, the functional group at the 2'-position of ribose infrequently interacts directly with the target molecule, but in many cases, it is of no relevance, and can be substituted by another modified molecule. Hence, an aptamer, unless the functional group involved in the direct binding to the target molecule is substituted or deleted, often retains the activity thereof. It is also important that the overall three-dimensional structure does not change substantially.

By predicting the secondary structure using the MFOLD program, or by predicting the steric structure by X-ray analysis or NMR analysis, it is possible to predict to some extent which nucleotide can be substituted or deleted, and where to insert a new nucleotide, without substantially affecting the three-dimensional structure of an aptamer. A predicted aptamer with the new sequence can easily be chemically synthesized, and it can be determined whether or not the aptamer retains the activity using an existing assay system.

Some embodiments of the invention are directed to specific aptamers that have already been identified. For example, in some embodiments, the aptamer comprises a sequence selected from the group consisting of:

```
Aptamer 1:
                                        (SEQ ID NO: 1)
GACGAGCTAAGAACCTTTAGGAGTGGAAA;

Aptamer 2:
                                        (SEQ ID NO: 2)
CCGTAGCTACGACGGAGGAAACTATGTTA;

Aptamer 3:
                                        (SEQ ID NO: 3)
AAAGCTCCTTGGAATAGTCTAATACCGGA;
```

```
-continued
Aptamer 4:
                                       (SEQ ID NO: 4)
TGTGTATAAAGGGGCGGTGAAAAGCGAAT;

Aptamer 5:
                                       (SEQ ID NO: 5)
AGAACTGGCCTTACTACGAAAAGTCCTTG;

Aptamer 6:
                                       (SEQ ID NO: 6)
CCAAAAGAATAAGACAACTAGGTAAGCTTT;

Aptamer 7:
                                       (SEQ ID NO: 7)
ACTTTGGGCCGTAACGATTAGTGCCCCTCT;

Aptamer 8:
                                       (SEQ ID NO: 8)
AAAAGCTCCTTGGAATAGTCTAATACCGGA;
and Aptamer 9:
                                       (SEQ ID NO: 9)
AGAACTGGCCTTACTACGAAAAGTCCTTGG,
``` or a homolog or analog thereof. In further embodiments, the aptamer comprises a sequence selected from the group consisting of SEQ ID NOS. 1-3, or a homolog or analog thereof.

The invention includes aptamers having nucleic acid sequences that are substantially homologous to nucleic acids that have been identified using an aptamer screening procedure, such as SEQ ID NOs 1-9. By substantially homologous, it is meant, a degree of primary sequence homology in excess of 80%. However, in further embodiments, the degree of homology can be at least 85%, at least 90%, or at least 95%. Homology is determined after aligning the sequences and introducing gaps, if necessary, to achieve the maximum percent homology. Homologous aptamers should also still exhibit the ability to specifically bind to target cells, such as tumor initiating cells, brain cancer cells, or glioblastoma cells. Preferably, the homologous aptamers have a binding affinity that is within two orders of magnitude of the affinity of the aptamers including SEQ ID NOs 1-9. It is well within the skill of those of ordinary skill in the art to determine whether a given sequence is substantially homologous to those specifically described herein, and has sufficient affinity for the target cells.

Preparation and Identification of Aptamers

The process of identifying suitable aptamers begins with the synthesis of a very large oligonucleotide library consisting of randomly generated sequences of fixed length flanked by constant 5' and 3' ends that serve as primers. The nucleic acids used to generate the library can be prepared using chemical techniques, for example, the phosphotriester method of Matteuccie, et al., J. Am. Chem. Soc. 103:3185 (1981) can be used to generate DNA sequences. Methods for the preparation of nucleic acid combinatorial libraries are known to those skilled in the art. See Markiewicz et al., Farmaco, 55(3), 174-7 (2000), the disclosure of which is incorporated herein by reference. Combinatorial libraries used for identification of suitable aptamers include a large number of different sequences; e.g., $10^{14}$-$10^{15}$ different sequences. Combinatorial libraries including a large number of random nucleic acid sequences suitable for screening are commercially available from a number of providers such as TriLink BioTechnologies™.

Aptamers having specific binding to a target cell or molecule can be identified using various methods known to those skilled in the art, such as the SELEX method or through a process known as in vitro selection. For example, the SELEX process is described in U.S. Pat. No. 5,475,096 and U.S. Pat. No. 5,270,163, the disclosures of which are incorporated herein by reference, and generally includes the following series of steps.

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to mimic a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The present invention includes preparation of aptamers that are specific for tumor initiating cells or brain cancer cells. In some embodiments, the brain cancer cells are glioblastoma cells. All of these types of cells are described further herein.

In some embodiments, the nucleic acid of the aptamer is complexed or linked to a functional substance bound thereto. The bond between the aptamer and the functional substance can be a covalent bond (i.e., the aptamer is linked) or a non-covalent bond (i.e., the aptamer is complexed). Methods of complexing or linking aptamers to functional substances are known to those skilled in the art. See Barbas et al., Future Oncol., 6(7), 1117-26 (2010), the disclosure of which is incorporated herein by reference. The complex or linked aptamer can be one wherein the aptamer of the present invention and one or more (e.g., 2 or 3) of functional substances of the same kind or different kinds are bound together. The functional substance is not particularly limited, as far as it newly confers a certain function to an aptamer of the present invention, or is capable of changing (e.g., improving) a certain characteristic which an aptamer of the present invention can possess. However, in some embodiments, the functional substance can be an anticancer agent or an imaging agent.

In some embodiments, the aptamer is complexed or linked to an imaging agent. Examples of imaging agents include fluorescent compounds, radioactive isotopes, and MRI contrast agents. For example, in some embodiments, the imaging agent is a fluorescent molecule for fluorescent imaging. The imaging agent can be any material having a detectable physical or chemical property. Such imaging agents have been well-developed in the field of fluorescent imaging, magnetic resonance imaging, positive emission tomography, or immunoassays and, in general, most any imaging agent useful in such methods can be applied to the present invention. Thus, an imaging agent is any composition detectable by spectroscopic, photochemical, biochemical, immunochemical, electrical, optical or chemical means. Means of detecting imaging agents are well known to those of skill in the art. Thus, for example, where the imaging agent is a radioactive compound, means for detection include a scintillation counter or photographic film as in autoradiography. Where the imaging agent includes a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label.

Further more specific examples of imaging agents include magnetic beads (e.g. Dynabeads™), fluorescent dyes (e.g., fluorescein isothiocyanate, AlexaFluor555, Texas red, rhodamine, and the like), radiolabels (e.g., $^3$H, $^{14}$C, $^{35}$S, $^{125}$I, $^{121}$I, $^{112}$In, $^{99m}$Tc), other imaging agents such as microbubbles (for ultrasound imaging), $^{18}$F, $^{11}$C, $^{15}$O, (for Positron emission tomography), $^{99m}$TC, $^{111}$In (for single photon emission tomography), and chelated lanthanides such as terbium, gadolinium (e.g., chelated gadolinium), and europium or iron (for magnetic resonance imaging). The choice of imaging agent depending on sensitivity required, ease of conjugation with the compound, stability requirements, available instrumentation, and disposal provisions.

In some embodiments, the aptamer is complexed or linked to an anticancer agent. Associating the anticancer with an aptamer specific for brain cancer cells (e.g., glioblastoma cells or tumor initiating cells) allows for better delivery of the anticancer agent to brain cancer cells, in order to provide increased antitumor activity and/or the ability to make use of lower doses of the anticancer agent. Anticancer agents such as alkylating agents can be readily incorporated into nucleic acids, and intercalating agents can be readily complexed to nucleic acids. Examples of anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof.

In some embodiments, the anticancer agents used are selected from those that have been approved for use in treating brain cancer. Examples of anticancer agents demonstrated to be effective against brain cancer include Everolimus, Bevacizumab, Procarbazine, Carmustine, Lomustine, and Temozolomide. However, in some embodiments, compounds such as Irinotecan, Cisplatin, Carboplatin, Methotrexate, Etoposide, Bleomycin, Vinblastine, Actinomycin, Cyclophosphamide, or Ifosfamide can be also be used to treat brain cancer.

In some embodiments, the functional substance is complexed or linked to the aptamer indirectly through use of a polymeric carrier such as a nanoparticle or a hydrogel. In addition to associating the functional substance with the aptamer, use of a polymeric carrier can also improve the pharmacokinetic and pharmacodynamic properties of the aptamers. Favorable changes include increased resistance to degradation by nucleases, decreased filtration by the kidneys, and decreased exposure to the immune system.

The aptamer compositions of the invention can be complexed or linked to a nanocarrier, preferably a polymeric nanocarrier such as a poly(lactide-coglycolide) PLGA nanoparticle. In some embodiments, the aptamer can be linked to the outside of the nanocarrier to allow for binding to target cells, while the anticancer agent or imaging agent is carried within the nanocarrier. For a description of nanocarrier-aptamer conjugates suitable for use with the aptamers of the present invention, see Zhou et al., Proc Natl Acad Sci USA., 110(29, 11751-6 (2013), and Farokhzad et al., Expert Opin Drug Deliv., 3(3), 211-24 (2006), the disclosures of which are incorporated herein by reference.

The aptamer compositions of the invention may be also complexed or linked with polyalkylene glycol ("PAG") moieties. Examples of PAG-derivatized nucleic acids are found in U.S. patent application Ser. No. 10/718,833, filed on Nov. 21, 2003, which is herein incorporated by reference in its entirety. Typical polymers used include poly(ethylene glycol) ("PEG"), also known as poly(ethylene oxide) ("PEO") and polypropylene glycol (including poly isopropylene glycol). Additionally, random or block copolymers of different alkylene oxides (e.g., ethylene oxide and propylene oxide) can be used in many applications PAG polymers suitable for therapeutic indications typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., J. Org. Chem., 60:331-336 (1995). PAG conjugates are often used not only to enhance solubility and stability but also to prolong the blood circulation half-life of molecules.

The ability of PAG to alter the biodistribution of a therapeutic is related to a number of factors including the apparent size (e.g., as measured in terms of hydrodynamic radius) of the conjugate. Larger polymers (>10 kDa) are known to more effectively block filtration via the kidney and to consequently increase the serum half-life of small macromolecules (e.g., peptides, antisense oligonucleotides). The ability of PEG to block filtration has been shown to increase with PEG size up to approximately 50 kDa (further increases have minimal beneficial effect as half life becomes defined by macrophage-mediated metabolism rather than elimination via the kidneys).

Aptamers that are linked or complexed with PAG are typically between 5 and 80 kDa in size however any size can be used, the choice dependent on the aptamer and application. In other embodiments, the size is between 10 and 80 kDa in size or between 10 and 60 kDa in size. In further embodiments, the PAG moieties are PEG ranging from 10, 20, 30, 40, 50, 60, or 80 kDa in size. In some embodiments, the PEG is linear PEG, while in other embodiments, the PEG is branched PEG. In still other embodiments the PEG is a 40 kDa branched PEG. In some embodiments the 40 kDa branched PEG is attached to the 5' end of the aptamer.

The present invention also encompasses PEG-linked multimeric oligonucleotides, e.g., dimerized aptamers. In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site.

Use of Aptamers for Cancer Treatment and Imaging

Aptamers of the present invention can be used as, for example, a pharmaceutical or a diagnostic reagent, or as test reagents. In particular they are useful for treating or imaging tumor initiating cells or brain cancer, including glioblastoma.

In some embodiments, the aptamer specifically binds to tumor initiating cells. Tumor initiating cells, also called cancer stem cells or tumor propagating cells, are functionally defined through assays of self-renewal and tumor propagation. See Reya et al., Nature, 414:105-11 (2001) and Hjelmeland et al., Nature Neuroscience, 14, 1375-81 (2011), the disclosures of which are incorporated herein by reference. In some embodiments, the aptamer specifically binds to tumor initiating cells found in brain cancer or glioblastoma. These cells share characteristics including bidirectional interplay with supportive vascular critical for maintenance of undifferentiated stated and survival, and stimulate angiogenesis through growth factor secretion. Several surface TIC markers have shown promise in brain cancer, and glioblastoma in particular.

Aptamers that are linked or complexed to anticancer agents can be used for the treatment of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression. Examples of cancers are sarcoma, breast, lung, brain, bone, liver, kidney, colon, and prostate cancer.

Brain cancer refers to an intracranial solid neoplasm or tumor found in the brain or the central spinal canal. They are created by an abnormal and uncontrolled cell division, usually in the brain itself, but also in lymphatic tissue, in blood vessels, in the cranial nerves, in the brain envelopes (meninges), skull, pituitary gland, or pineal gland. Tumors can be benign or malignant, can occur in different parts of the brain, and may or may not be primary tumors. A primary tumor is one that has started in the brain, as opposed to a metastatic tumor, which is something that has spread to the brain from another part of the body. The incidence of metastatic tumors are more prevalent than primary tumors by a ratio of 4:1. Tumors may or may not be symptomatic: some tumors are discovered because the patient has symptoms, others show up incidentally on an imaging scan, or at an autopsy. The most common primary brain tumors, listed in the order corresponding to their prevalence, are glioblastoma, meningiomas, pituitary adenomas, and nerve sheath tumors. Symptoms of brain tumors are well known to those skilled in the art. The preferred method for diagnosing a brain tumor is the use of imaging.

In some embodiments, the aptamer specifically binds to glioblastoma cells. Glioblastoma involves glial cells, and include four subtypes, which are proneural, neural, mesenchymal, and classical glioblastoma. See Verhaak et al., Cancer Cell 17 (1): 98-110 (2010). Ninety-seven percent of tumors in the 'classical' subtype carry extra copies of the Epidermal growth factor receptor (EGFR) gene, and most have higher than normal expression of Epidermal growth factor receptor (EGFR), whereas the gene TP53, which is often mutated in glioblastoma, is rarely mutated in this subtype. In contrast, the proneural subtype often has high rates of alterations in TP53, and in PDGFRA, the gene encoding a-type platelet-derived growth factor receptor, and in IDH1, the gene encoding isocitrate dehydrogenase-1. The mesenchymal subtype is characterized by high rates of mutations or other alterations in NF1, the gene encoding Neurofibromatosis type 1 and fewer alterations in the EGFR gene and less expression of EGFR than other types. Many other genetic alterations have been described in glioblastoma, and the majority of them are clustered in three pathways, the P53, RB, and the PI3K/AKT.

The aptamers of the present invention may be routinely adapted for diagnostic purposes according to any number of techniques employed by those skilled in the art. Diagnostic utilization may include both in vivo or in vitro diagnostic applications. Diagnostic agents need only be able to allow the user to identify the presence of a given target at a particular locale or concentration. Simply the ability to form binding pairs with the target may be sufficient to trigger a positive signal for diagnostic purposes in some embodiments. Those skilled in the art would also be able to adapt any aptamer by procedures known in the art to incorporate an imaging agent in order to track the presence of brain cells, glioblastoma cells, or tumor initiating cells. The imaging agents used will vary depending on the intended imaging methodology being used.

In one aspect, the invention provides a method of imaging brain cancer cells in a subject. The method includes administering an effective amount of an aptamer consisting of a single stranded nucleic acid having 100 nucleotides or less that specifically binds to brain cancer cells, the aptamer being complexed or linked to an imaging agent, to the subject and detecting the aptamers with an imaging apparatus. In other embodiments, the invention provides a method for imaging tumor initiating cells, or glioblastoma cells.

In order to generate an image of the tissue region, it is necessary for an effective amount of imaging agent to reach the tissue region of interest, but it is not necessary that the imaging agent be localized in this region alone. However, in some embodiments, the aptamer complexed or linked to an imaging agent is targeted or administered locally such that they are present primarily in the tissue region of interest. When used to detect or image cancer cells in a cell culture, one skilled in the art should be able to vary the exposure time, the amount of loaded virus particle and the final concentration to optimize the detection or imaging desired. Other experimental parameters may be varied to achieve the other effect, depending on the specific experiment conducted, and identification of such parameters should involve minimal experimentation by those skilled in the art.

Examples of images that can be produced through the use of aptamers include two-dimensional cross-sectional views and three dimensional images. In some embodiments, a computer is used to analyze the data generated by the imaging agents in order to generate a visual image. The tissue region can be an organ of a subject such as the heart, lungs, or blood vessels. In other embodiments, the tissue region can be diseased tissue, or tissue that is suspected of being diseased, such as a tumor or atherosclerotic tissue. Examples of imaging methods include computed tomography, positive emission tomography, and magnetic resonance imaging, and optical or fluorescence imaging, all of which have imaging apparatus associated with their use.

The compositions of the invention can be used for the imaging and detection of target cells in vitro (e.g., cell culture) and in vivo. The compositions of the invention can also be used for the imaging and detection of target cells in organs and tissues ex vivo. Examples of target cells include tumor initiating cells, brain cancer cells, and glioblastoma cells.

Another aspect of the invention provides a method of treating cancer in a subject. The method includes administering an effective amount of an aptamer consisting of a single stranded nucleic acid having 100 nucleotides or less that specifically binds to cancer cells, the aptamer being complexed or linked to an anticancer agent, to the subject. Examples of cancer that can be treated include cancer including tumor initiating cells, brain cancer, and glioblastoma.

Suitable subjects benefiting from the methods of the present invention include male and female mammalian subjects, including humans, non-human primates, and non-primate mammals. Other suitable mammalian subjects include domesticated farm animals (e.g., cow, horse, pig) or pets (e.g., dog, cat). In some embodiments, the subject includes any human or animal subject who has a disorder characterized by unwanted, rapid cell proliferation. Such disorders include, but are not limited to cancers and precancers, such as those including tumor initiating cells, brain cancer, and glioblastoma. For methods of prevention the subject is any human or animal subject, and preferably is a human subject who is at risk of obtaining a disorder characterized by unwanted, rapid cell proliferation, such as cancer. The subject may be at risk due to exposure to carcinogenic agents, being genetically predisposed to disorders characterized by unwanted, rapid cell proliferation, and so on.

Administration of Aptamers

The medicament of the present invention can be one formulated with a pharmaceutically acceptable carrier. As examples of the pharmaceutically acceptable carrier, excipients such as sucrose, starch, mannitol, sorbitol, lactose, glucose, cellulose, talc, calcium phosphate, and calcium carbonate; binders such as cellulose, methylcellulose, hydroxylpropylcellulose, polypropylpyrrolidone, gelatin, gum arabic, polyethylene glycol, sucrose, and starch; disintegrants such as starch, carboxymethylcellulose, hydroxylpropylstarch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin-ammonium salt, glycine, and orange powder; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not imitative.

Preparations suitable for oral administration are a solution prepared by dissolving an effective amount of ligand in a diluent such as water, physiological saline, or orange juice; capsules, sachets or tablets comprising an effective amount of ligand in solid or granular form; a suspension prepared by suspending an effective amount of active ingredient in an appropriate dispersant; an emulsion prepared by dispersing and emulsifying a solution of an effective amount of active ingredient in an appropriate dispersant, and the like.

The aptamers can be coated by a method known per se for the purpose of taste masking, enteric dissolution, sustained release and the like as necessary. As examples of coating agents used for the coating, hydroxypropylmethylcellulose, ethylcellulose, hydroxymethylcellulose, hydroxypropylcellulose, polyoxyethylene glycol, Tween 80, Pluronic F68, cellulose acetate phthalate, hydroxypropylmethylcellulose phthalate, hydroxymethylcellulose acetate succinate, Eudragit (manufactured by Rohm, Germany, methacrylic acid/acrylic acid copolymer), pigments (e.g., ferric oxide red, titanium dioxide lo and the like) and the like are used. The medicament may be a rapid-release preparation or sustained-release preparation. Examples of the base of the sustained-release preparation include liposome, atelocollagen, gelatin, hydroxyapatite, PLGA and the like.

As preparations suitable for parenteral administration (e.g., intravenous administration, subcutaneous administration, intramuscular administration, topical administration, intraperitoneal administration, intranasal administration, pulmonary administration and the like), aqueous and non-aqueous isotonic sterile injectable liquids are available, which may comprise an antioxidant, a buffer solution, a bacteriostatic agent, an isotonizing agent and the like. Aqueous and non-aqueous sterile suspensions can also be mentioned, which may comprise a suspending agent, a solubilizer, a thickener, a stabilizer, an antiseptic and the like. The preparation can be included in a container such as an ampoule or a vial in a unit dosage volume or in several divided doses. An active ingredient and a pharmaceutically acceptable carrier can also be freeze-dried and stored in a state that may be dissolved or suspended in an appropriate sterile vehicle just before use. In addition to liquid injections, inhalants and ointments are also acceptable. In the case of an inhalant, an active ingredient in a freeze-dried state is micronized and administered by inhalation using an appropriate inhalation device. An inhalant can be formulated as appropriate with a conventionally used surfactant, oil, seasoning, cyclodextrin or derivative thereof and the like as required.

The dosage of the medicament of the present invention varies depending on the kind and activity of active ingredient, seriousness of disease, animal species being the subject of administration, drug tolerability of the subject of administration, body weight, age and the like, and the usual dosage, based on the amount of active ingredient per day for an adult, can be about 0.0001 to about 100 mg/kg, for example, about 0.0001 to about 10 mg/kg, preferably about 0.005 to about 1 mg/kg.

The following examples are included for purposes of illustration and are not intended to limit the scope of the invention.

EXAMPLES

Example 1

Aptamer Identification of Brain Tumor Initiating Cells

Aptamers are short nucleic acids capable of specific and tight binding to target structures that can include proteins, lipids, other nucleic acids or any three-dimensional structures. Aptamers are named from the Latin aptus ("fitting") and Greek meros ("part"). Aptamers can be selected by the in vitro iterative process SELEX (Systematic Evolution of Ligands by EXponential enrichment) that enriches for RNA or DNA aptamers capable of discriminating between molecular targets with even subtle differences. Tan et al., Trends in biotechnology, 29:634-40 (2011); Yang et al., Advanced drug delivery reviews, 63:1361-70 (2011). Cell-SELEX is a modified procedure that uses cells as an evolutionary selection source and does not require foreknowledge of a molecular target. Ye et al., Int. J. Mol. Sci., 13:3341-53 (2012). In general, cell-SELEX is a combination of in vitro evolution and combinatorial chemistry involving a series of steps including incubation, partitioning, and amplification.

In Cell-SELEX, the initial pool of library is chemically created by solid-phase technology. This library must contain at least one, but preferably several, sequences(s) having the unique folded conformations required to facilitate selective binding with the target. Cell-SELEX typically involves positive selection to isolate target cell-interacting sequences and counter selection to eliminate non-specific sequences recognizing non-target cells. Counter selection results in the depletion of aptamers which bind common cell surface receptors in the resulting pools. Thus, the probability of recognizing unique molecules exclusively expressed in the target population is greatly enhanced. Aptamers bind to their targets with high affinity with typical binding dissociation constants (Kd) in the pM to nM range. Further, aptamers are structurally stable under a wide range of temperature and storage conditions while instantly reconstituting their active tertiary structures in some conditions. Aptamers can be synthesized quickly and cost-effectively with minimal inter-batch variability, in contrast to monoclonal antibodies. Aptamers can also be easily modified to increase stability and affinity for therapeutic and diagnostic purposes. Donovan et al., Methods in molecular biology, 764:141-52 (2011); Huang et al., Analytical chemistry, 80:567-72 (2008).

Materials and Methods

Isolation and Culture of Cells Including TICs

To obtain the large numbers of cells necessary for Cell-SELEX, TICs were derived from pooled tumors of the same parental GBM xenograft. Tumors were dissociated using the Worthington Biochemical Papain Dissociation System according to the manufacturer's instructions. To facilitate recovery from enzymatic digestion, cells were then cultured in Neurobasal Media supplemented with B27 without vitamin A (Invitrogen™), basic Fibroblast Growth Factor (bFGF; 10 ng/ml) and Epidermal Growth Factor (EGF; 20 ng/ml) for at least six hours prior to magnetic sorting using microbead-conjugated CD133 antibodies (Miltenyi Biotech). CD133 enriched cultures functionally validated in assays of self-renewal and tumorigenesis designated as TICs were utilized as targets to enrich for TIC-specific aptamers and were maintained in the above stem cell media. CD133 negative cells depleted for tumorigeneic or self-renewing capacity were utilized as non-stem glioma cells (non-TICs) and cultured in the presence of 10% fetal bovine serum. Human neural progenitors were commercially obtained (Lonza).

DNA Primers and Library

The DNA library used for TIC-specific aptamer Cell-SELEX was a pool of DNA sequences consisting of a combination of common and unique nucleotides. 19 common nucleotides were present on the 5' end, 50 randomized base sequences in the middle, and an additional 18 common nucleotides on the 3' end. The 5' end was labeled by fluorescein isothiocyanate (FITC) (5' FITC-sequence-N45-sequence 3') to monitor enrichment of selection using FACS. The forward primer was labeled at the 5' end with FITC (5' FITC-sequence 3') and the reverse primer with biotin at the 5' end (5' Biotin-sequence 3'). To amplify each eluted pool, PCR was used, and single strand DNA was isolated by capturing the biotinylated complementary strand by streptavidin-biotin interactions and denaturing double strand DNA with 200 mM NaOH. PCR mixtures were prepared and PCR reactions were performed according to the manufacturer's instructions.

Cell-SELEX

TICs isolated from pooled 08-387 xenografts were used as target (positive cell) and matching non-TICs were used for counter selection (negative cell). Five nmol of DNA library was dissolved in 1000 µL of binding buffer containing 4.5 g/liter glucose, 5 mM $MgCl_2$, 0.1 mg/ml tRNA and 1 mg/ml BSA in Dulbecco's PBS. The DNA library or enriched pool was denatured at 95° C. for 5 min, cooled on ice for 10 min, and incubated with TICs on ice in an orbital shaker for 1 hour. After TICs were washed three times to remove unbound DNA sequences, the bound DNA sequences were eluted using 500 µL binding buffer at 95° C.

for 10 min with centrifugation. To perform a counter selection, each aptamer pool was incubated with non-TICs for 1 hour, and then the supernatant was collected to perform the positive selection. Pool enrichment was monitored using FACS and subjected to cloning into *Escherichia coli* using TOPO TA cloning Kit for sequencing (Invitrogen™) to identify the aptamer candidates.

Flow Cytometry to Monitor Aptamer Binding

Each FITC-labeled aptamer candidate was incubated with TICs or non-TICs in binding buffer on ice for 30 min. The cells were washed three times with binding buffer, and the pellets with the bound sequences were resuspended in 200 µL binding buffer. The fluorescence intensity was determined with a LSR II (BD Immunocytometry Systems) by counting 10,000 events. The FITC-labeled unselected single strand DNA library was used as a negative control. To determine the specificity of the selected aptamers, aptamer binding to additional GBM cells (08-322, 4121, U87MG) or neural progenitors (RenCell c-myc immortalized human neural progenitors, Millipore; human fetal neural progenitors, Lonza) was determined. For determination of aptamer binding to differentiated TICs, TICs were plated on Geltrex-coated plates in the presence of 10% serum and harvested after five days for FACS analysis.

Determination of Aptamer Affinity for TICs

To determine the binding affinity of the aptamers, target cells ($1\times10^6$) were incubated with varying concentrations of FITC-labeled aptamer or library and analyzed by flow cytometry. The mean fluorescence intensity of the unselected library was subtracted from that of the aptamer with the target cells to determine the specific binding of the labeled aptamer. The apparent equilibrium dissociation constant (Kd) of the aptamer-cell interaction was obtained by fitting the dependence of intensity of specific binding on the concentration of the aptamers to the equation $Y=B \max X/(kd+X)$.

Isolation and In Vitro Characterization of Aptamer$^{high}$ and Aptamer$^{low}$ GBM Cells After overnight recovery of GBM cells from tissue dissociation, each Cy5-labeled aptamer was incubated with each specimen for 30 min. After washing thrice, labeled GBM cells were subjected to cell sorting. For the sphere formation assay, 10 cells of either aptamer$^{high}$ and aptamer$^{low}$ GBM cells sorted by FACS were directly plated into each well of a six well plate containing 200 µL of TIC culturing medium similar to our prior descriptions. After 10 to 14 days, the number of tumorspheres in each well was counted and plotted. For the cell proliferation assay, aptamer$^{high}$ and aptamer$^{low}$ GBM cells were sorted into each 15 mL tube, and equal numbers of cells were plated into 96 wells. Differences in cell growth were measured using Cell-Titer Glow (Promega™) according to the manufacturer's instructions and prior reports. Hjelmeland et al., PLoS biology, 8:e1000319 (2010); Li et al., Cancer cell, 15:501-13 (2009).

In Vivo Tumorigenic Potential

To determine tumorigenic potential, 300 or 3000 viable aptamer$^{high}$ or aptamer$^{low}$ GBM cells were intracranially injected into athymic/nude immunocompromised mice as we have previously described. Animals were maintained until the development of neurological signs including lethargy, seizure, ataxia, or paralysis or for a maximum of 60 days, when they were sacrificed. All animal procedures were performed in accordance with a Cleveland Clinic IACUC approved protocol.

Results

SELEX Screening Against TICs Enriched for a Pool of Aptamers

Figure 1:
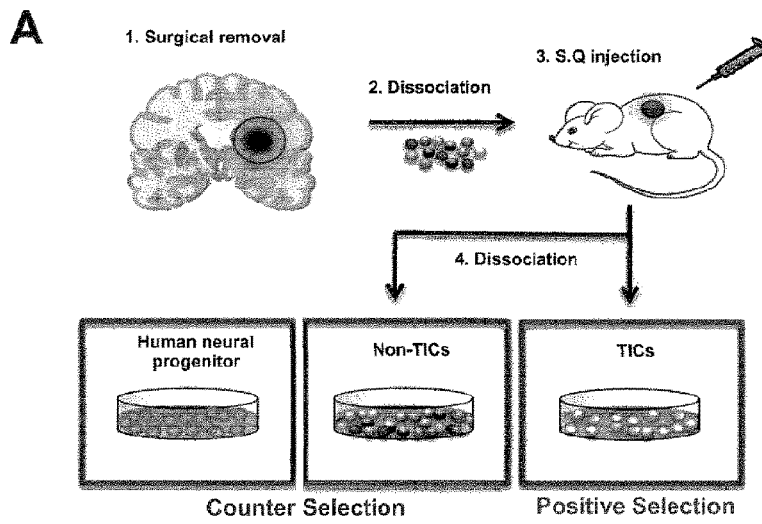
FIG. 1 provides schemes and graphs showing how TIC-specific aptamer candidates were identified from Cell-SELEX. (A) To develop TIC-specific aptamers, GBM cells were obtained from subcutaneous xenografts initiated from a GBM patient specimen. To obtain enough cells for experiments, cells dissociated from multiple xenografts of GBM1 (08-387) cells were pooled. TICs and non-TICs prospectively sorted from these xenografts using CD133 were used for positive or counter selection respectively. To enhance the cancer-specific activity of selected aptamers, human neural progenitor cells were also used for counter selection step. (B) As the number of rounds of enrichment increased, more stringent selection conditions were applied to increase the specificity and affinity of the TIC-specific aptamers identified. These conditions included increasing the number of non-TICs, decreasing the number of TICs, increasing the concentration of competitor, and decreasing the incubation period. (C) FACS analysis confirmed that a pool of aptamers present after 8 rounds of selection was enriched with DNA sequences which bind to TICs but have minimal binding to non-TICs or normal neural progenitors. (D) DNA sequencing of the DNA sequences present in the pool of aptamers enriched after selection revealed nine different sequences with more than two copy numbers from ninety-six clones.
Figure 1:
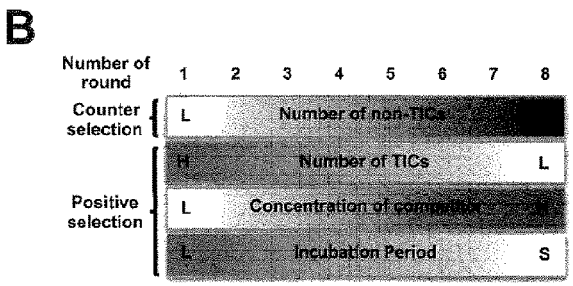
Figure 1:
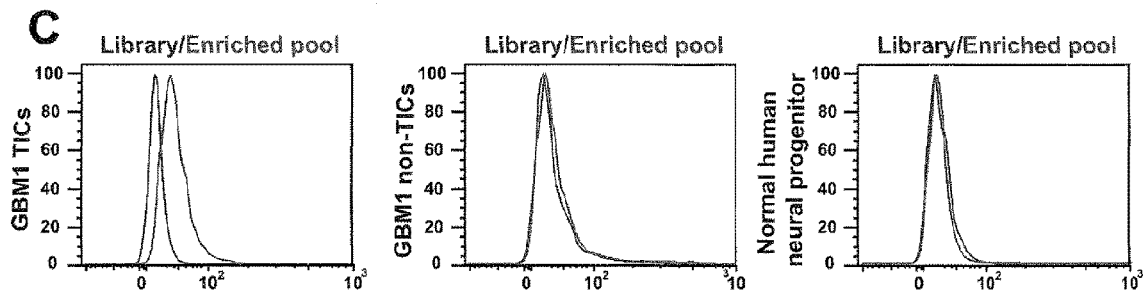

Systematic evolution of ligands by exponential enrichment (SELEX) is a method of repeated rounds of in vitro selection used to identify DNA or RNA aptamers which bind specific targets. Pu et al., Analytical and bioanalytical chemistry, 397:3225-33 (2010); Sefah et al., Nature protocols, 5:1169-85 (2010). To identify TIC-specific aptamers, a library of randomized DNA sequences was exposed to subgroups of GBM cells isolated from pools of xenografts originally generated from a human GBM specimen (FIG. 1A). Aptamers were first exposed to non-TICs or nonneoplastic human neural progenitors (NPCs) as a counter selection to eliminate sequences not specific for TICs. DNA sequences which did not bind NPCs or non-TICs were incubated with TICs to select for binding aptamers as a positive selection (FIG. 1A). To select highly specific aptamers to TICs with high affinity, the number of human neural progenitors and non-TICs was increased while the number of TICs was decreased in the subsequent rounds of enrichment (FIG. 1B). In addition, concentration of competitors was increased while the reaction time decreased to further enrich for high affinity TIC-specific aptamers (FIG. 1B). Eight rounds of selection enriched a pool of DNA sequences preferentially bound TICs in comparison to non-TICs and NPCs as determined via flow cytometry with fluorescently labeled aptamers (FIG. 1C). Having confirmed the ability of the enriched DNA pool to recognize TICs, we then cloned and sequenced the enriched DNA pool to identify individual TIC-specific aptamer candidates. We obtained nine DNA sequences which were repeatedly detected in multiple colonies of bacteria out of 96 colonies analyzed for sequencing. The most frequent sequence domains repeated 8 to 27 times (FIG. 1D; Table 1). Table 1 provides the complete sequences for A1-A6 (designated A1C-A6C) while only the repeated sequence domains for A1-A9 are shown in FIG. 1D.

TABLE 1

Complete TIC-enriched Aptamer Sequences

| | |
|---|---|
| A1C; SEQ ID NO: 10 | 5' ATCCACGAGTGACGCAGCACAGAGTGGAAGACGAGCT AAGAACCTTTAGGAGTGGAAAAGATAGCTCATGGACACGG TGGCTTAGT 3' |
| A2C; SEQ ID NO: 11 | 5' ATCCACGAGTGACGCAGCATGTTTAGGAAACCGTAGC TACGACGGAGGAAACTATGTTAAACATCCCCATGGACACG GTGGCTTAGT 3' |
| A3C; SEQ ID NO: 12 | 5' ATCCACGAGTGACGCAGCACGAGCAACACAAAAGCTC CTTGGAATAGTCTAATACCGGAGCGAGAAAGCTGGACACG GTGGCTTAGT 3' |
| A4C; SEQ ID NO: 13 | 5' ATCCACGAGTGACGCAGCACAGTGATCAGTTGTGTAT AAAGGGGCGGTGAAAAGCGAATTCCAGTCGACTGGACACG GTGGCTTAGT 3' |
| A5C; SEQ ID NO: 14 | 5' ATCCACGAGTGACGCAGCACCGAGAGGAGAGAACTGG CCTTACTACGAAAAGTCCTTGGTTGCCAGGGGTGGACACG GTGGCTTAGT 3' |
| A6C; SEQ ID NO: 15 | 5' TCCACGAGTGACGCAGCACGTGAGTAAACCAAAAGAA TAAGACAACTAGGTAAGCTTTGCAAGGGTAGTGGACACGG TGGCTTAGT 3' |

Individual Aptamers Bind TICs

To confirm the ability of individual aptamer candidates to specifically bind TICs, flow cytometry was performed with fluorescine isothiocyanate (FITC)-labeled individual aptamer candidates (FIG. 1D, sequences A1C-A6C) and compared to signal obtained from FITC labeled library containing randomized DNA sequences as a negative control. A positive shift along the FITC axis was observed with each TIC enriched aptamer compared to the library when incubated with TICs isolated from GBM1. In contrast, negligible shifts in the histogram occurred with non-TICs isolated from the same tumor or TICs differentiated with fetal bovine serum. Similar preferences for aptamer binding to TICs in comparison to matched non-TICs was observed for cells derived from two additional GBM xenografts for the majority of the aptamers tested. TIC-enriched aptamers also failed to bind to the well-characterized U87MG GBM cell line, which was passaged under pro-differentiating conditions in serum. To further characterize the ability of the aptamers to bind non-neoplastic cells in the brain, flow cytometry was also performed with ReNCell CX immortalized human neural progenitors or primary human fetal neural progenitors. The majority of the TIC-enriched aptamers showed minimal binding to nonneoplastic neural progenitors, although A4 bound both sets of non-neoplastic brain cells, indicating some of the aptamers could more broadly recognize neural progenitors.

Figure 2:
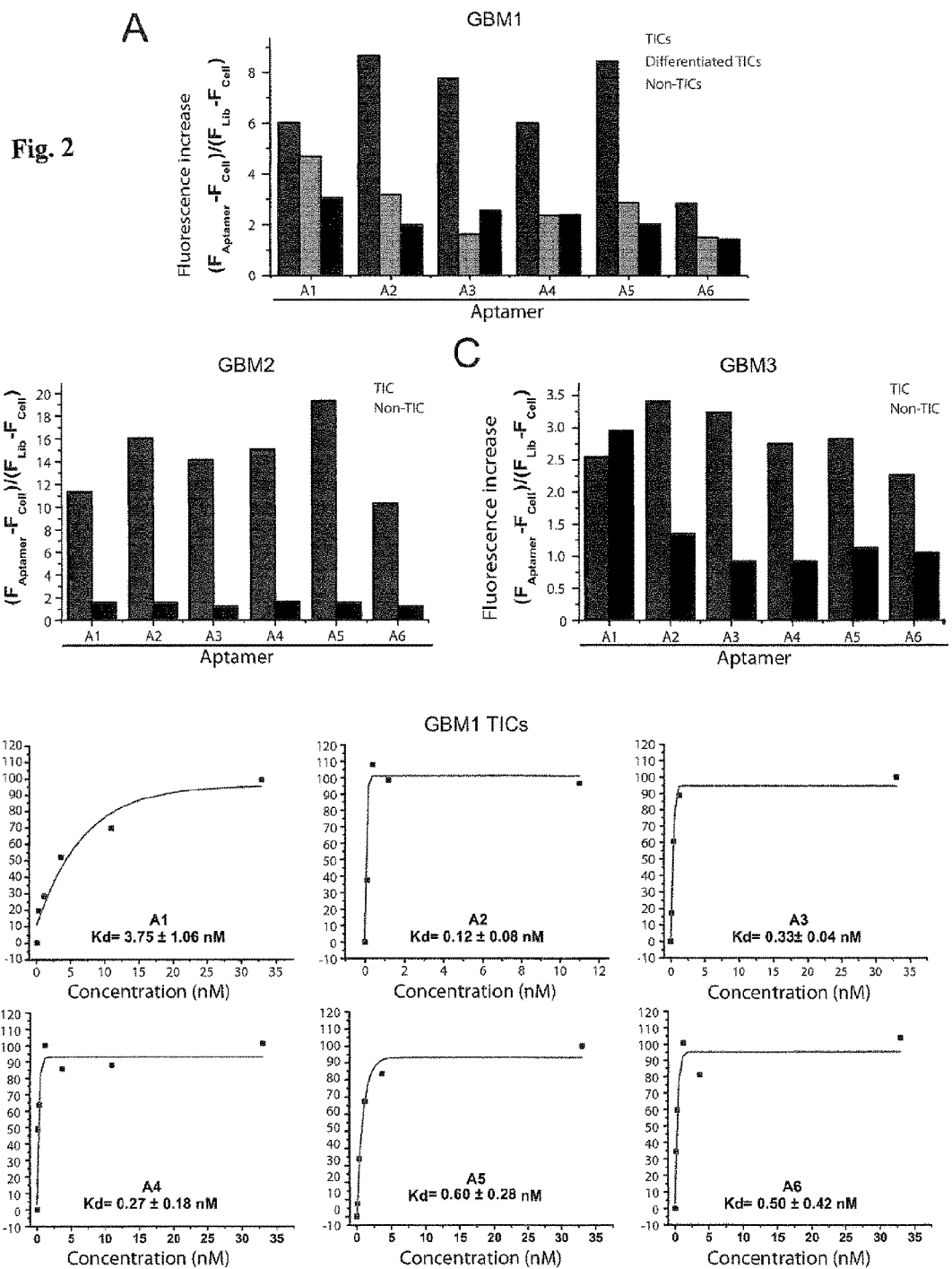
FIG. 2 provides graphs showing that aptamer candidates bind with high affinity to TICs. FACS analysis was performed using fluorescent aptamers with TICs, non-TICs, and differentiated TICs isolated from (A) GBM1 (08-387), (B) GBM2 (4121), or (C) GBM3 (08-322) xenografts. Fluorescence shift was calculated using the equation $(F_{aptamer} - F_{cell})/(F_{library} - F_{cell})$. $F_{aptamer}$, $F_{library}$, $F_{cell}$ refers to the fluorescence value with the aptamer, library, and cell itself. (D) The equilibrium dissociation constant (Kd) of the aptamer-cell interaction was obtained by fitting the dependence of intensity of specific binding on the concentration of the aptamers to the equation $Y = B \max X/(kd+X)$.

To further evaluate the specificity of TIC-enriched aptamers, the fold change in fluorescence was calculated. Fluorescence shift was calculated using the equation $(F_{aptamer} - F_{cell})/(F_{library} - F_{cell})$, where $F_{aptamer}$, $F_{library}$ and $F_{cell}$ refers to the fluorescence value of the aptamer, library, and cell itself. Using this calculation, specificity of aptamers A2-A6 for TICs in comparison to non-TICs was shown for all three GBMs tested (FIG. 2A-C). A1 also showed greater binding to TICs in GBM1 and GBM2, but not GBM3 (FIG. 2A-C). The affinity of A1-A6 binding to TICs was also very high with dissociation constants (KD) in the nM range (FIG. 2D). Together, these data strongly suggest that we have identified several aptamers that specifically bind TICs with high affinity.

Figure 3:
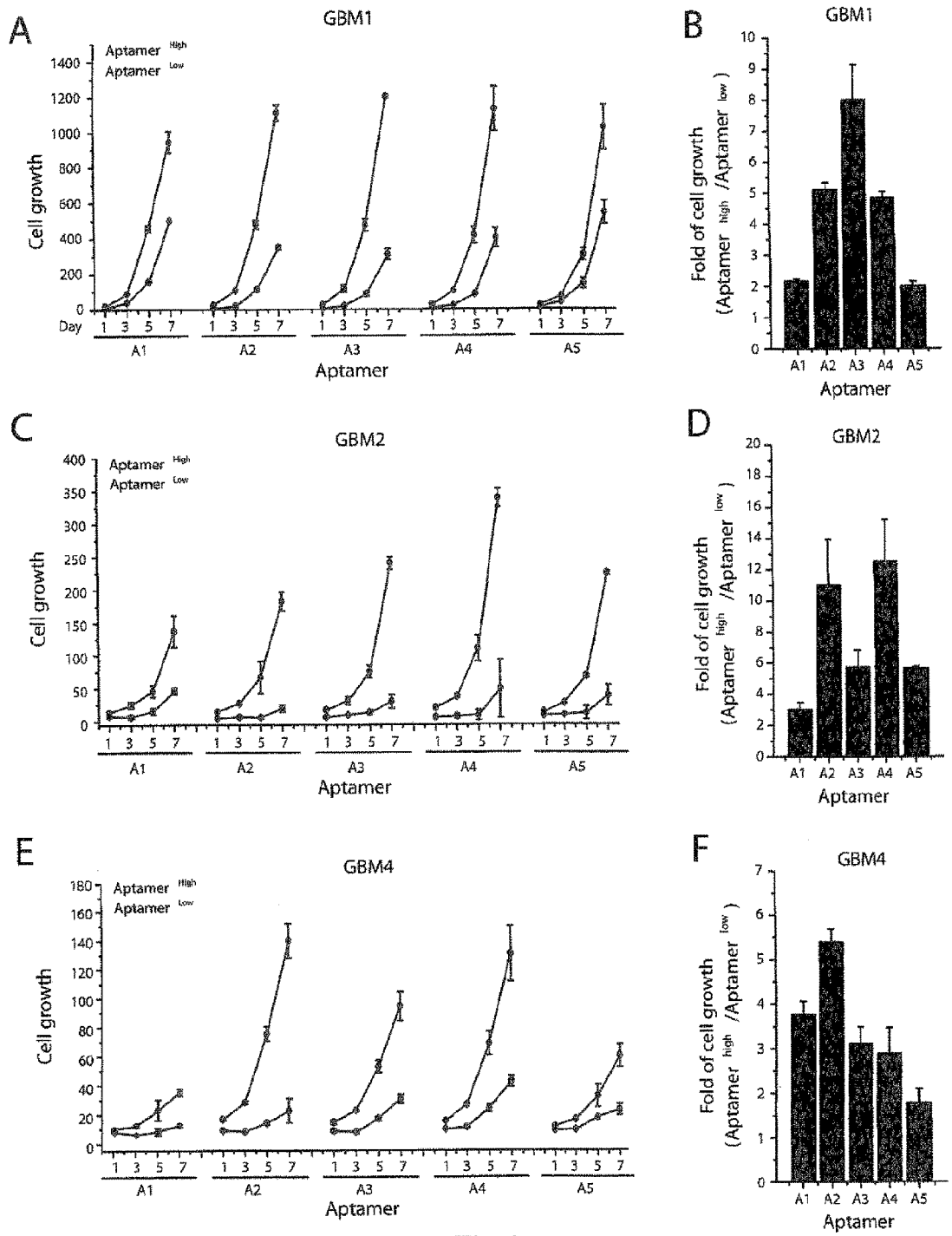
FIG. 3 provides graphs showing that aptamer$^{high}$ cells were enriched for cell growth in vitro. FACS analysis was used to segregate aptamer$^{high}$ and aptamer$_{low}$ cells from (A,B) GBM1 (08-387), (C,D) GBM2 (4121), and (E,F) GBM4 (3691) xenografts. (A, C, E) Cells were plated at equivalent density and growth measured over time using the Cell Titer assay. (B, D, F) The fold change in proliferation between aptamer$^{high}$ cells aptamer$^{low}$ cell is displayed.

TIC Specific Aptamers Enrich for GBM Cells with Increased Growth and Tumorsphere Formation Capacity As TICs are functionally defined, we examined the ability of the TIC-enriched aptamers to identify cells that could proliferate and self-renew. Individual Cyanine Dye 5 (Cy5) labeled aptamers A1-A5 were used to segregate aptamer-high and aptamer-low fractions from bulk cells isolated from GBM xenografts. In cell titer assays, each of the five aptamerhigh fractions (A1-A5) demonstrated significantly enhanced cell growth over time in the three GBMs tested (FIG. 3). The greatest differences were observed for A2, A3, and A4, resulting in 3 to 12 fold enhancement in cell growth (FIG. 3).

Figure 4:
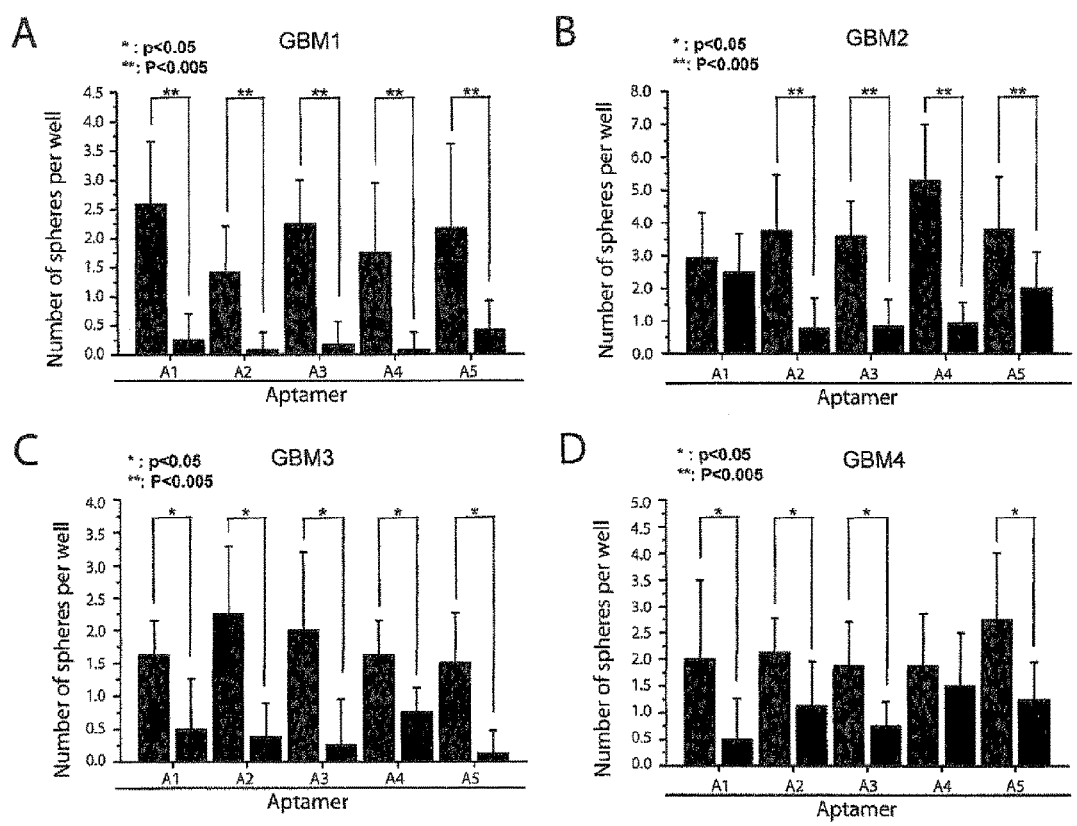
FIG. 4 provides graphs showing that aptamer$^{high}$ cells are enriched for neurosphere formation capacity. FACS analysis was used to segregate aptamer$^{high}$ and aptamer$^{low}$ cells from (A) GBM1 (08-387), (B) GBM2 (4121), (C) GBM3 (08-322) and (D) GBM4 (3691) xenografts and cells plated for neurosphere formation assays. The number of spheres per well is shown.

As neurosphere formation assay has been used as a surrogate measure of self-renewal, we used this assay to determine if TIC-binding aptamers could enrich GBM cells with self-renewing capacity. We found that A2, A3, and A5 significantly segregated cells with neurosphere formation capacity in all four GBMs tested (FIG. 4). A1 and A4 enriched cells also demonstrated greater neurosphere formation capacity in three of four GBMs tested (FIG. 4). The data demonstrate that TIC enriched aptamers can be used to segregate fractions of GBM cells with TIC properties as measured in vitro.

Aptamer$^{high}$ Cells are Enriched for Tumorigenic Potential

Figure 5:
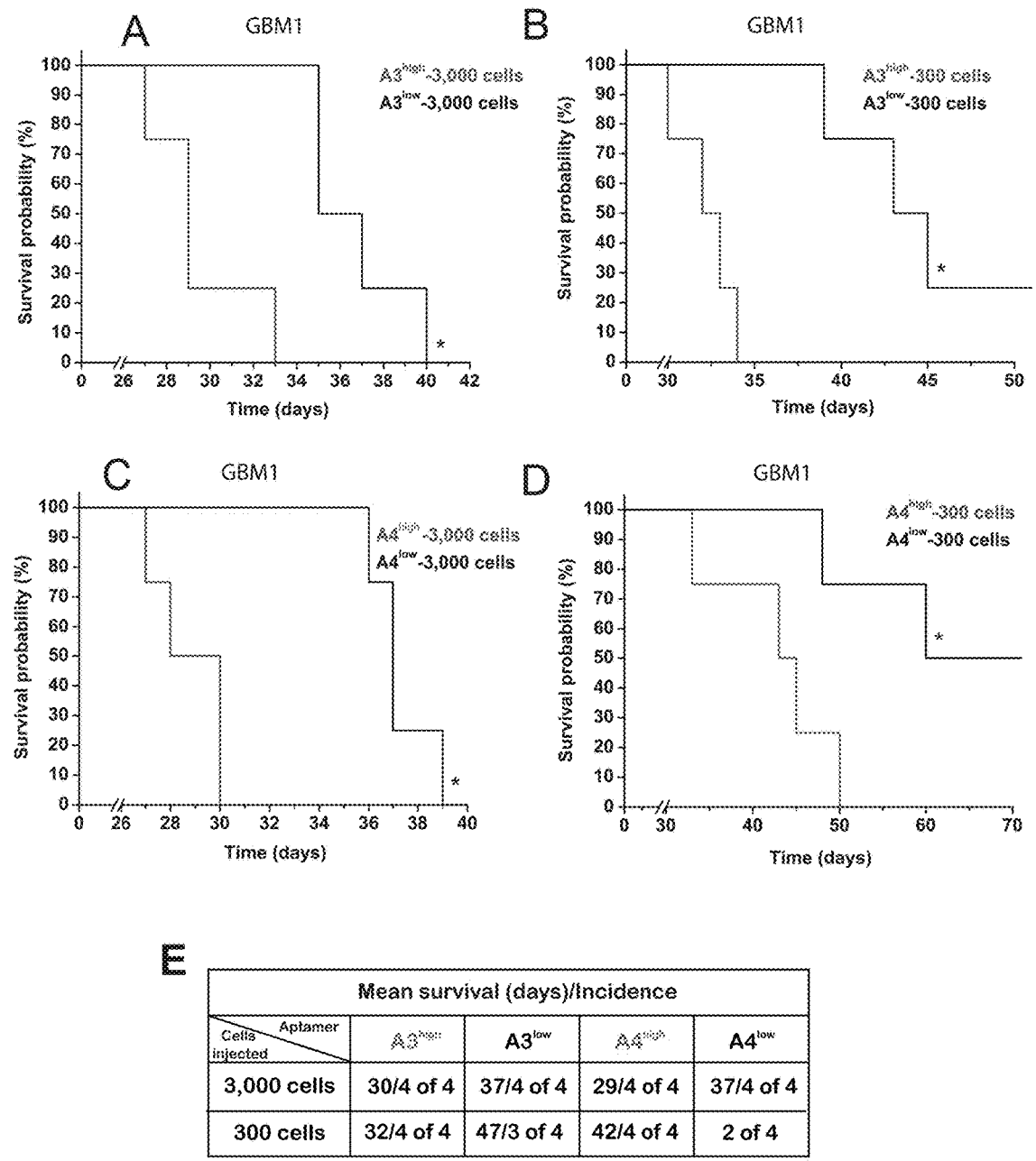
FIG. 5 provides graphs showing that aptamer$^{high}$ cells were enriched for tumorigenic potential in comparison to aptamer$_{low}$ cells. FACS analysis was used to segregate aptamer$^{high}$ and aptamer$^{low}$ cells from GIBM1 (08-387) using A$_3$ (A,B) or A4 (C,D). 3000 or 300 of matched aptamer$^{high}$ or aptamer$^{low}$ cells were isolated and transplanted into mouse brains intracranially and their neurological signs were monitored and (A-D) Kaplan Meier survival curves shown. (E) Mean survival as well as tumor incidence are also displayed.

As TICs by definition must be able to propagate the parental tumor in vivo, we determined whether the TIC-specific aptamers could segregate for differences in tumorigenic potential. Using Cy5 labeled A3 (FIG. 5A, 5B) and A4 (FIGS. 5A, 5B) as probes, aptamer$^{high}$ and aptamer$^{low}$ fractions were sorted from bulk cells isolated from GBM1 xenografts. 3000 (FIG. 5A, 5C) or 300 (FIG. 5B, 5D) live aptamer$^{high}$ and aptamer$^{low}$ cells were implanted into the brains of immunocompromised mice which were then monitored daily for neurologic signs. The survival of mice injected with either A3 or A4 aptamer$^{high}$ cells was significantly reduced with decreased mean survival (FIG. 5E). All mice injected with the lower number of aptamer$^{high}$ cells (300) developed tumors, whereas 3 of 4 tumors developed with A3 aptamer$^{low}$ cells and only 2 of 4 tumors developed with A4 aptamer$^{low}$ cells (FIG. 5E). These data suggest TIC enriched aptamers can segregate for GBM cells with tumorigenic potential.

Figure 6:
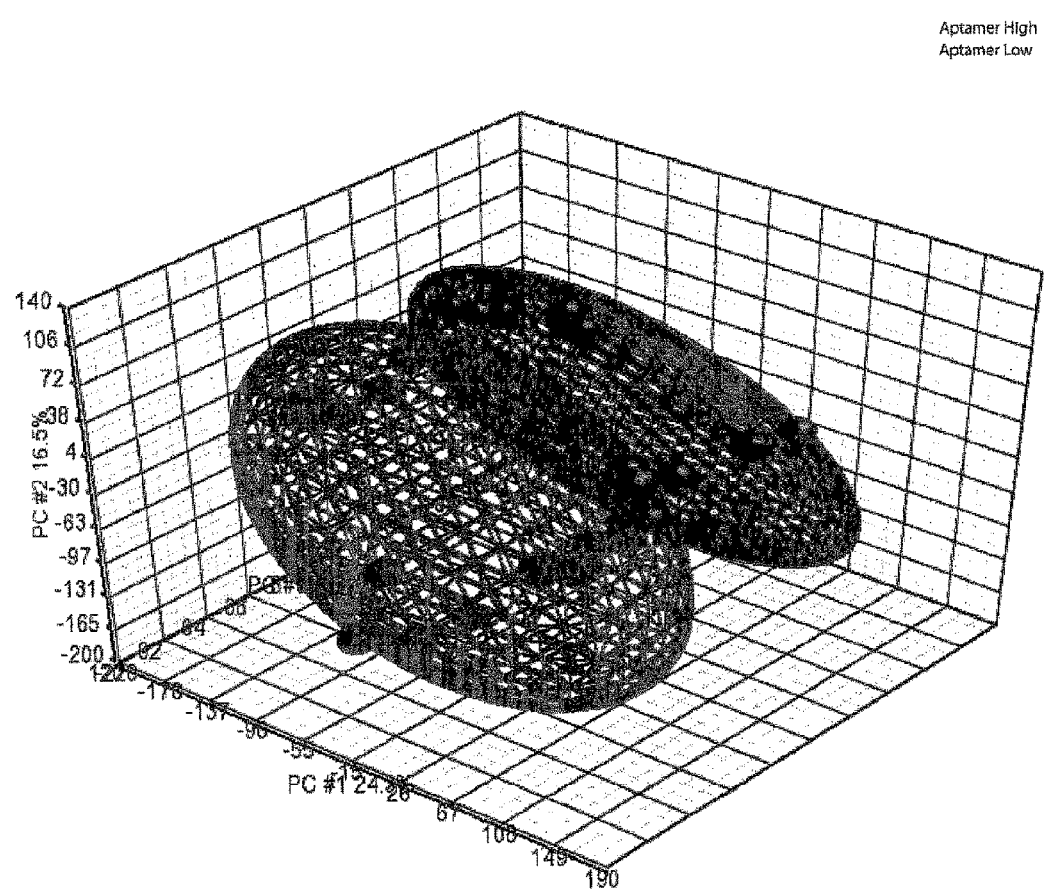
FIG. 6 provides a graph showing that principal component analysis reveals similarities in aptamer$^{high}$ and aptamer$^{low}$ cells. FACS analysis was used to segregate aptamer$^{high}$ and aptamer$^{low}$ cells from GBM1 (08-387), GBM2 (4121), and GBM4 (3691) xenografts using fluorescently labeled aptarners A1, A2, A3, A4, or A5. The data for the aptamer$^{high}$ fractions from all xenografts was pooled and compared to data for the corresponding group of aptamer$^{low}$ cells. Principal component analysis comparing these aptamer$^{high}$ and aptamer$^{low}$ groups recognized two distinct groups of data as indicated by the ellipsoids.

Principal Component Analysis Demonstrates Aptamer$^{high}$ and Aptamer$^{low}$ Cells are Distinct Having demonstrated that the TIC-enriched aptamers could segregate for functional measures of TIC biology, we sought to determine if there were similarities in the molecular profile of aptamer$^{high}$ or aptamer$^{low}$ cells as determined via gene expression and principal component analysis (PCA). PCA is a multivariate analysis resulting in a three-dimensional visual representation of the data useful for identifying similarities within large datasets. We utilized FACS analysis with fluorescently labeled aptamers (A1-A5) in GBM1, GBM2, and GBM4 xenografts to segregate aptamer$^{high}$ and aptamer$^{low}$ cells. Microarray data from the aptamer$^{high}$ and aptamer$^{low}$ populations for each of the individual aptamers in each of the cell types (total of 15 datasets with matched aptamer$^{high}$ and aptamer$^{low}$ cells) was then processed via PCA. The resulting analysis showed two distinct groups (shown as ellipsoids) corresponding aptamer$^{high}$ and aptamer$^{low}$ datasets (FIG. 6). The PCA analysis therefore indicates the data from the aptamer$^{high}$ and aptamer$^{low}$ cells is distinct demonstrating different molecular profiles between the groups.

Figure 7:
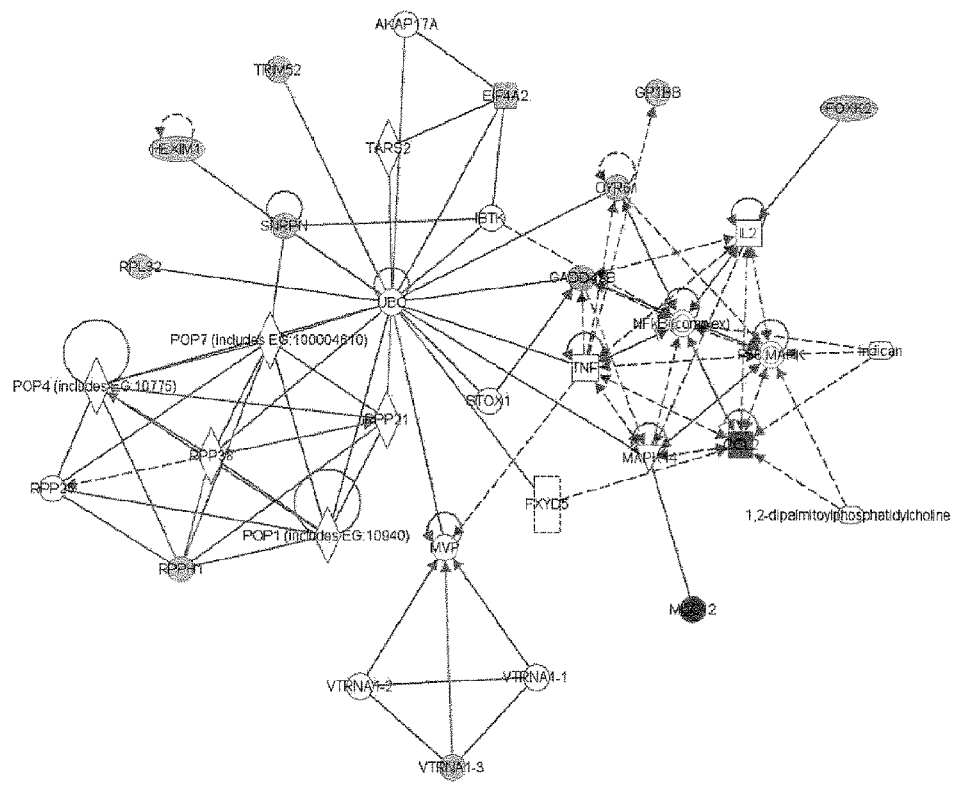
FIG. 7 provides a scheme showing the cellular development, hematological system development and function, hematopoiesis network for the commonly differentially expressed genes for Aptamer 3 high vs. low cells shown in Table 2. Aptamer3$^{high}$ cells have a differential genetic profile associated with downregulation of genes involved in cellular development. FACS analysis was used to segregate aptamer$^{high}$ and aptamer$^{low}$ cells from (A) GBM1 (08-387), (B) GBM2 (4121), and (C) GBM4 (3691) xenografts using fluorescently labeled A3. Harvested RNA was used for microarray analysis on an Affymetrics platform and Ingenuity software used to identify genes commonly differentially expressed between A3$^{high}$ and A3$^{low}$ cells which are shown. The genes differentially expressed in the same direction across all GBMs tested were then used to create a database which was analyzed in Ingenuity to identify the top network containing these targets.

Aptamer$^{high}$ Cells are Enriched for Molecular Signatures Associated with the Regulation of Cellular Development To identify specific molecular differences between aptamer$^{high}$ and aptamer$^{low}$ cells, microarray data from GBM1, GBM2, and GBM4 cells segregated with A3 (FIG. 7) or A4 fluorescently labeled aptamers was further analyzed. Comparison of genes differentially elevated or repressed in $A_3^{high}$ cells in comparison to $A3^{low}$ cells, revealed a set of 27 molecules that were commonly altered across all three lines (Table 2). Only one gene transcript, chemokine (C-C motif) ligand 2 (CCL2) was consistently elevated whereas the expression of the remaining 26 targets were repressed in $A3^{high}$ cells (Table 2). A similar analysis of $A_4^{high}$ cells in comparison to $A4^{low}$ cells, identified a set of 25 targets whose expression levels were commonly altered across all three GBM cultures tested. DEAD box polypeptide 60 was commonly elevated, whereas expression in the remaining targets were repressed in $A_4^{high}$ cells. When the A3 or A4 gene expression profiles were analyzed using Ingenuity software, the top biological networks represented by these profiles were both found to regulate cellular development (FIG. 7). In fact, several genes were commonly downregulated in the $A_3^{high}$ and $A_4^{high}$ enriched cells indicating that independent TIC-specific aptamers can select a sub-fraction of GBM cells with common phenotypes and some similarities in their expression profiles.

TABLE 2

Commonly Differentially Expressed Genes for Aptamer High vs. Low Cells

| SYMBOL | GENE NAME | 387 | 4121 | 3691 |
| --- | --- | --- | --- | --- |
| CCL2 | chemokine (C-C motif) ligand 2 | 2.38 | 2.04 | 2.73 |

TABLE 2-continued

Commonly Differentially Expressed Genes
for Aptamer High vs. Low Cells

| SYMBOL | GENE NAME | 387 | 4121 | 3691 |
|---|---|---|---|---|
| EIF4A2 | eukaryotic translation initiation factor 4A2 | −2.03 | −2.19 | −3.38 |
| DCAF4L1 | DDB1 and CUL4 associated factor 4-like 1 | −2.07 | −2.30 | −2.07 |
| OR2B6 | olfactory receptor, family 2, subfamily B, member 6 | −2.16 | −2.22 | −2.10 |
| LOC388692 | uncharacterized LOC388692 | −2.24 | −2.28 | −2.20 |
| SNORD77 | small nucleolar RNA, C/D box 77 | −2.42 | −2.49 | −2.43 |
| GP1BB | glycoprotein ib (platelet), beta polypeptide | −2.69 | −2.26 | −2.96 |
| RPL32 | ribosomal protein L32 | −2.79 | −2.03 | −1.81 |
| CYR61 | cysteine-rich, angiogenic inducer, 61 | −2.94 | −2.03 | −1.58 |
| FOXK2 | forkhead box K2 | −2.97 | −2.39 | −1.94 |
| LOC349196 | uncharacterized LOC349196 | −3.01 | −2.01 | −2.06 |
| TRIM52 | tripartite motif containing 52 | −3.03 | −2.08 | −1.88 |
| C9orf131 | chromosome 9 open reading frame 131 | −3.05 | −2.25 | −2.08 |
| REXO1L1 | REX1, RNA exonuclease 1 homolog (S. cerevisiae) - like 1 | −3.09 | −2.25 | −2.43 |
| RPPH1 | ribonuclease P RNA component H1 | −3.23 | −2.10 | −2.40 |
| VTRNA1-3 | vault RNA 1-3 | −3.33 | −2.25 | −1.80 |
| OR4F16 | olfactory receptor, family 4, subfamily F, member 16 | −3.37 | −2.74 | −1.64 |
| mir-320 | microRNA 320a | −3.63 | −2.22 | −1.93 |
| SNRPN | small nuclear ribonucleoprotein polypeptide N | −4.13 | −2.13 | −1.99 |
| GADD45B | growth arrest and DNA-damage-inducible, beta | −4.53 | −2.70 | −3.34 |
| HEXM1 | hexamethylene bis-acetamide inducible 1 | −5.87 | −2.10 | −2.55 |
| HIST1H2AG | histone cluster 1, H2ag | −7.73 | −2.39 | −2.54 |
| FAM71A | family with sequence similarity 71, member A | −8.04 | −2.18 | −4.61 |
| DNM1P46 | DNM1 pseudogene 46 | −8.37 | −2.00 | −3.59 |
| HIST2H2BE | histone cluster 2, H2be | −8.92 | −2.08 | −1.72 |
| LOC100287178 | ubiquitin carboxyl-terminal hydrolase 17-like | −15.01 | −2.08 | −8.10 |
| MUC12 | mucin 12, cell surface associated | −20.19 | −7.18 | −5.46 |

Discussion

GBMs rank among the most lethal of human cancers, and median survival remains 12-15 months despite the advanced standard of care, including surgical resection followed by radiotherapy and chemotherapy with the DNA-alkylating agent temozolomide. The highly infiltrative and invasive feature of GBMs hinders complete resection of most tumors, and recurrence is nearly universal. TICs are thought to be the portion of GBM cells which are responsible for both cellular invasion and therapeutic resistance, indicating the need for therapies which kill these cells and for imaging reagents which can identify them in vivo. We believe that the TIC-specific aptamers identified in this study may help to fill these needs by providing methods to better target TICs for detection and treatment.

One method through which the TIC-enriched aptamers identified here may be developed for clinical use is through conjugation to increase the affinity and specificity of therapeutic nanoparticles for subgroups of cancer cells which drive tumor maintenance. Nanoparticle technology has already been approved by the FDA to treat patients with breast cancer in the form of Nab-paclitaxel, and paclitaxel loaded nanoparticles demonstrated efficacy against GBM cell lines. Gao et al., Biomaterials, 33, 5115-23 (2012). Paclitaxel loaded nanoparticles cross the blood brain barrier and reduce GBM growth in animal models, suggesting the potential of enhancing the efficacy of these reagents through conjugation to TIC-specific aptamers. Guo et al., Biomaterials, 32:8010-20 (2011). Alternatively, cisplatin was delivered via aptamers in prostate cancer models (Dhar et al., PNAS, 108:1850-5 (2011)) and demonstrated efficacy against high-grade gliomas with intrarterial administration (Zustovich et al., Anticancer research, 29:4275-9 (2009)) although high toxicities have been reported. Aptamer-drug conjugates for delivery of doxorubicin (Huang et al., Chembiochem, 10:862-8 (2009)) have recently been shown to have efficacy with liposomal mediated delivery in GBM animal models. Yang et al., Nanomedicine, 8:81-92 (2012). Postoperative/chemo-radiotherapy with doxorubicin liposomes was well tolerated in phase II clinical trials with liposomal delivery, but did not have significant improvement in outcome over historical averages. Beier et al., BMC cancer, 9:308 (2009). Directed delivery to TICs through conjugating to TIC-specific aptamers may generate more promising results. These data suggest that TIC-targeting aptamers conjugated to nanoparticles may provide additional benefit for GBM therapies.

In addition to therapeutic utility, labeled TIC-specific aptamers may be useful as imaging reagents. In GBM, tumor recurrence most often occurs within two centimeters of the primary resection site, indicating the difficulty of complete resection of the tumor cells due to their infiltrating behavior. The ability to visualize invasive cells during surgery could therefore provide significant benefit. Fluorescent dyes encapsulated in nanoparticles have demonstrated some success for crossing the blood-brain barrier to serve as imaging reagents in glioma, and quantum dot-labeled nanoparticles with aptamers targeting tenascin-C on human glioma cells have demonstrated the ability to image glioma cells in vitro. Chen et al., Nanotechnology, 19:235105 (2008). Recently Hwang et al. demonstrated the ability to use MRI, fluorescent imaging, and radionucleotide imaging together to visualize tumors after treatment of mice bearing C6 glioma xenografts with radiolabeled nanoparticles containing rhodamine and a cancer-targeting aptamer (against nucleolin). Hwang et al., J. Nucl. Med., 51:98-105 (2010). Although intracranial tumors were not imaged, the data suggest the utility of aptamer conjugated nanoparticles as promising for imaging reagents.

In addition to the ability to either identify or target TICs, aptamers could have many potential applications for brain tumor biology which have not yet been fully explored. For example, aptamers could be identified which specifically recognize proneural, mesenchymal, or classical glioblastoma (GBM) subtypes allowing for rapid profiling of patient biopsies. Aptamers which recognize GBM cells in specific regions of the tumor associated with therapeutic resistance, such as the hypoxic niche, could also be identified and be useful for directing therapies to these difficult to target areas. Even aptamers demonstrating specificity for non-neoplastic neural stem cells can be useful as these cells are being considered for delivery of anti-glioma therapies.

TIC specific aptamers also serve as a powerful tool to delineate critical molecular mechanisms in GBM. We have used microarray analysis to determine a set of genes which are differentially regulated in aptamer$^{high}$ cells. These studies identified common targets which were involved in pathways associated with the regulation of cellular development and have recognized roles in cancer. For example, CCL2 which was elevated in the aptamer$^{high}$ cells is implicated in an interleukin-6 dependent paracrine loop to promote cellular invasion in vivo (Zhang et al., Carcinogenesis, 33:312-9 (2012)) and has been linked to the promotion of a cancer stem cell phenotype through interferon regulatory factor 7. Jin et al., Brain, 135:1055-69 (2012). Neutralizing antibodies against CCL2 have also demonstrated efficacy in xenografts models as an anti-glioma therapy. Zhu et al., Journal of neuro-oncology, 104:83-92 (2011). Hexamethylene bisacetamide-inducible protein 1 (HEXIM1) promotes the stability of p53 and inhibits metastasis, suggesting that the reduced expression levels present in aptamer$^{high}$ cells would promote tumorigenesis. Lew et al., JBC, 287:36443-54 (2012). Growth arrest and DNA damage-inducible 45b (GADD45b) is a cellular stress sensor which is suggested to be a tumor suppressor, confirming it would be beneficial for cancer cells to have decreased GADD45b expression as shown in our study. Ying et al., Clin Cancer Res., 11:6442-9 (2005). Furthermore, GADD45b has been shown to be over-expressed in non-side population cells depleted for cancer stem cell characteristics in embryonic carcinoma cells, consistent with the notion it is enriched in TICs. Inowa et al., Stem cells international, 2010:782967 (2010). Thus, our molecular analysis suggests TICs identified with specific aptamers have gene expression profiles which could promote tumorigenesis.

Example 2

Use of Aptamer-Conjugated Nanoparticles for Anti-TIC Therapy

Direct local delivery of chemotherapy to brain tumors makes it possible to bypass the blood-brain barrier and achieve adequate interstitial drug concentrations at the tumor site, without producing high systemic drug levels. Currently, this can be accomplished utilizing a dime-size degradable wafer (Gliadel®) that is placed in the tumor resection bed following surgery. Gliadel® relies on diffusion of BCNU, the encapsulated drug, into the tissue as the wafers release the drug into the tumor cavity. A limitation of this approach is that high levels of active drug can be achieved only within a few millimeters of the wafer and cannot reach the areas of tumor cell infiltration in the surrounding brain (centimeters). To improve diffusion in brain tissue, convection-enhanced delivery (CED) technology is promising as it disperses agents via both convection and diffusion and is, therefore, able to deliver drugs over a large volume in the brain. Zhou et al., Cancer J., 18, 89-99 (2012). CED has also been previously attempted in GBM patients, including a recent clinical trial (PRECISE trial). This trial utilized CED of IL13 coupled with pseudomonas exotoxin to selectively bind with IL13 receptors present on tumor cells. This study failed to significantly improve survival over Gliadel®, in large part because free IL13-PE38QQR was administered in liquid medium that did not permit adequate distribution into the brain and was rapidly diluted into the spinal fluid. To overcome the limitations associated with drug delivery using wafers or CED of free drug solution, we propose combining CED and nanotechnology. In this scenario, nanoparticles of appropriate size can penetrate brain tissue over a large volume. On the other hand, nanoparticles are large enough to be trapped in the brain. Unfortunately, traditional approaches for CED of polymeric nanoparticles have been limited by the restricted penetration of nanoparticles in brain tissue.

Figure 8:
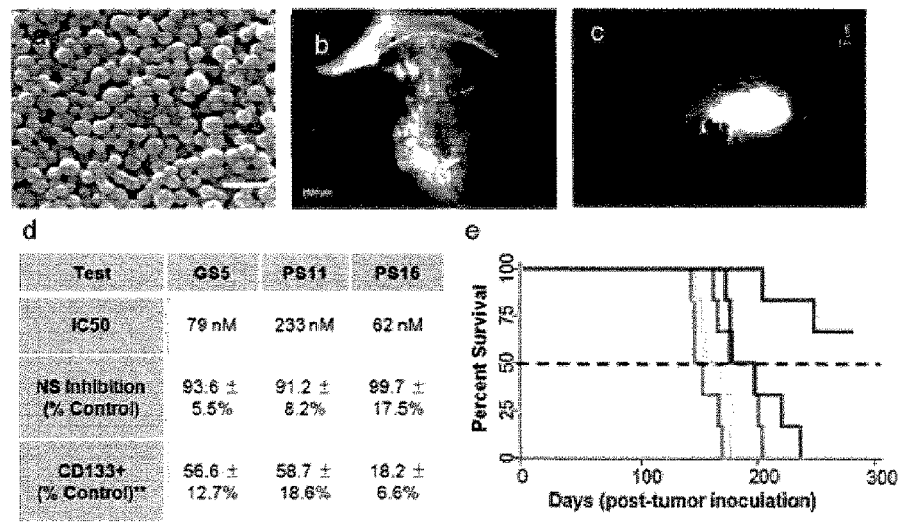
FIG. 8 provides images and data showing the synthesis and evaluation of brain-penetrating nanoparticles. (a). Morphology of nanoparticles. Scale bar=200 nm. (b). Representative fluorescence microscopy images of 2 mg coumarin 6

Recently, we made breakthroughs in synthesizing brain-penetrating nanoparticles (FIG. 8a), fabricating stepped catheters and delivering nanoparticles via CED. Zhou et al., Proc Natl Acad Sci USA., 110(29), 11751-6 (2013). These advances allow us to deliver nanoparticles over a clinically relevant volume: administration of 20 µl nanoparticle suspension in the rat brains resulted in an average distribution volume of 74±7 mm$_3$ ($V_d/V_i$=3.7) (FIG. 8b). Administration of 338 µl nanoparticle suspension in the pig brains resulted in an average distribution volume of 1180±37 mm$_3$ ($V_d/V_i$=3.5) (FIG. 8c). In both animals, resulting volume of diffusion is >3 times the volume of infused therapeutic agent ($V_d/V_i$>3), suggesting the distribution of nanoparticles in the brain is clinically relevant. We also developed a surface modification procedure through which biotinylated ligands can be efficiently conjugated to nanoparticles, and demonstrated surface modification through this approach did not alter distribution of nanoparticles in the brain. We further evaluated whether this drug delivery system can be used to treat TIC-derived tumors. To identify compounds selectively toxic to TICs, we screened a library of ~2,000 compounds that have been once approved for human uses (Chong et al., Nat Chem Biol 2, 415-416 (2006)) against GS5, a well-characterized TIC line (Wolpert et al., Journal of neuroimmunology 250, 27-34 (2012)), and identified 32 candidate drugs that were able to efficiently inhibit TIC proliferation and self-renewal. One compound in particular, the anti-helminthic cyanine dye dithiazanine iodide (DI), potently inhibited GS5 proliferation, with an IC50 of 79 nM. Treatment with DI inhibited GS5 sphere formation, a measure of TIC self-renewal, by 94%. Additionally, DI decreased the CD133+ cell population by 57% (FIG. 8d). DI was evaluated in two additional TIC lines isolated in our lab, PS11 and PS16, and showed similar anti-TIC effects (FIG. 8d). We successfully encapsulated DI into our brain-penetration nanoparticles, which were administered via a single infusion into rat brains bearing GS5-derived tumors. Brain-penetrating DI nanoparticles significantly increased the median survival of tumor-bearing rats (FIG. 8e). Kaplan-Meier analysis revealed that rats treated with brain-penetrating, DI-loaded nanoparticles had significant improvements in median survival, which was over 280 days. By contrast, rats receiving standard nanoparticles, free drug, blank/un-loaded nanoparticles and no treatment had a median survival of 180 days, 177 days, 156 days, and 147 days, respectively (p<0.005 for each comparison).

Our platform has several major advantages over currently available nanocarrier delivery systems. First, the polymer used for nanoparticle synthesis is poly(lactic-co-glycolic acid) (PLGA), which is known to have an excellent safety profile: PLGA was part of an FDA-approved formulation in 1969 and has been safely used in clinical practice since that time. Second, the release kinetics of PLGA nanoparticles can be more easily modulated than those of competing nanocarrier systems utilized in intracranial applications, namely liposomes and micelles. Third, the versatile surface modification approach described in this study enables rapid, modular attachment of biotinylated agents, thereby allowing for efficient labeling of nanoparticles with a host of cell-targeting and—penetrating agents. Finally, the exceptionally small diameters allow these nanoparticles to penetrate relatively large, clinically relevant volumes when delivered by CED.

Additionally, there are other avenues of aptamer conjugation that can be explored in order to determine the most effective platform for targeting and delivery in the brain tumor environment. Other groups have demonstrated successful delivery of payloads using poly(ethylene glycol) (PEG) and poly(caprolactone) (PCL) nanoparticles covalently modified with aptamers on the particle surface using 1-Ethyl-3-(3-dimethylaminopropyl)carbodiimide (EDC) attachment chemistry. Gao et al., Biomaterials, 33(26):6264-72 (2012). In preliminary data we have been able to successfully synthesize PEG-PCL nanoparticles with an average hydrodynamic radius of 44.70±1.8 nm, as measured by dynamic light scattering (DLS, FIG. 9a). We further characterized these nanoparticles by transmission electron microscopy (TEM), utilizing a negative staining protocol with phosphotungstic acid (PTA), and found general agreement with our DLS measurements (FIG. 9b). In order to measure covalent attachment of TIC-specific aptamers to the particle surface, we utilized DNA oligos modified with 6-carboxyfluorocein (6-FAM) on the C-terminus end of the strand. We then doped our PEG-PCL nanoparticles with bis-carboxy PEG. The presence of carboxyl groups provided attachment sites for the EDC reaction with the amine groups of the DNA. Following standard protocols, we covalently coupled the 6-FAM labeled TIC-specific aptamer to the PEG-PCL nanoparticles. Measured fluorescence of the nanoparticles indicated successful conjugation of aptamer to nanoparticle (FIG. 9c). Our approach holds several advantages. PEG and PCL are known to have an excellent safety profiles and are currently used in many FDA-approved biomaterial applications. The nanoparticle formulation technique also allows for easy encapsulation of dyes or small molecules, as has been demonstrated by Gao et al. (ibid). Furthermore, aptamer coupling is straight-forward and allows for covalent attachment of any aptamer sequence. Finally, the relatively small size of the nanoparticles would enhance penetration into brain tumors, similar to our PLGA nanoparticle formulation. We will modify this delivery and conjugation system by conjugating TIC-specific aptamers to nanoparticle surface and evaluate their anti-TIC effects in tumor xenografts.

Surface Conjugation with TIC-Specific Aptamers Enhances Therapeutic Effects of Drug Loaded Brain-Penetrating Nanoparticles.

Experiments are designed to synthesize aptamer-conjugated brain penetrating nanoparticles that recognize TICs in vivo and utilize these to deliver anti-GBM therapies. We will synthesize aptamer-conjugated brain-penetrating nanoparticles using the versatile surface modification approach that we developed. Specifically, TIC-specific and control aptamers will be synthesized, biotinylated and conjugated to brain-penetrating nanoparticles as we previously reported (FIG. 10). Zhou et al., Proc Natl Acad Sci USA, 110(29), 11751-6 (2013), the disclosure of which is incorporated herein by reference. Particle sizes will be measured with scanning electron microscopy (SEM) and dynamic light scattering (DLS).

Surface charge will be measured with ZetaPals. Next, we will determine whether aptamer-conjugation enhances cell uptake of nanoparticles in TICs. Fluorescence dye coumarin 6 (C6) will be encapsulated into nanoparticles. Uptake of nanoparticles conjugated with different aptamers will be evaluated on TICs directly isolated from patient specimens using flow cytometry. Aptamer-conjugated brain-penetration nanoparticles will be also tested for their penetration in brain tissue. The formulation demonstrating the highest affinity with TICs while maintaining their penetrating ability will be selected for therapeutic evaluation in TIC-derived tumor xenografts. DI, which demonstrated broad anti-TIC effects, will be encapsulated into nanoparticles. The ability of DI loaded aptamer-modified nanoparticles to reduce TIC percentages will be determined through both molecular and functional experiments. Additional studies will determine toxicity against normal NPCs in an effort to define a nanoparticle-aptamer conjugate therapeutic index.

PLGA Nanoparticle synthesis: To synthesize brain-penetrating nanoparticles loading with C6, DI or Alexa633, a single emulsion process will be used. Typically, C6 or DI or Alexa633 will be dissolved together with PLGA in 2 ml ethyl acetate. The mixed solution will be added dropwise to a solution of 4 ml 5% polyvinyl alcohol. The resulting emulsion will be sonicated on ice for 3×10 s. The mixture will then be added dropwise to a stirring solution of 0.3% PVA in water and the solvent will be allowed to evaporate from the mixture over five hours. Brain-penetrating nanoparticles will be collected through partial ultracentrifugation (typically over 10,000 g) and further washed three times with DI water, frozen at −80° C. overnight, and lyophilized, after which the particles will be stored at −20° C. To synthesize nanoparticles for surface modification, we will first conjugate avidin to palmitic acid as we previously reported. Fahmy et al., Biomaterials 26, 5727-5736 (2005) Avidin-displayed nanoparticles will be synthesized using the same procedures except inclusion of avidin-palmitic acid in 5% polyvinyl alcohol. Conjugation of biotinylated aptamers will be conducted in the last step of nanoparticle synthesis prior to lyophilization.

PEG-PCL Nanoparticle synthesis: To synthesize nanoparticles that could be easily coupled to DNA aptamers as well as encapsulate a payload, a solvent evaporation procedure will be performed. Bis-Carboxy PEG and PEG-PCL block copolymer will be dissolved at a ratio of 1:10 in 1 mL dichloromethane. The resulting solution will be added dropwise to 4 mL of 0.6% sodium cholate. The sample will then be probe sonicated on ice at 200 W for 3×10s. After sonication, the sample will be stirred for 5 min before transferred to a rotary evaporator. The solvent will be evaporated in this manner at 30° C. until bubbling (evidence of evaporation) has ceased. To conjugate aptamers to the particle surface, the carboxyl groups on the particles will first be activated by incubation in 2-(N-morpholino)ethanesulfonic acid (MES) buffer (pH 6.5) containing 200 mM EDC and 50 mM N-Hydroxysuccinimide (NHS) under gentle stirring for 60 min. After the incubation period, 50 μL of 100 μM 6-FAM labeled DNA aptamer will be added and the solution is stirred (covered) overnight. Sample cleanup is performed the following day by two rounds of ultracentrifugation (30 000 molecular weight cut-off) and washing with diH$_2$O. After the final wash, 10×DPB is added to the samples to a final concentration of 1× and stored at 4° C.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An aptamer consisting of a single stranded nucleic acid having 100 nucleotides or less and comprising a sequence selected from the group consisting of SEQ ID NOS. 1-9 or an analog thereof that specifically binds tumor initiating cancer cells.

2. The aptamer of claim 1, wherein the nucleic acid has 50 nucleotides or less.

3. The aptamer of claim 1, wherein the tumor initiating cancer cells are brain cancer cells.

4. The aptamer of claim 1, wherein the tumor initiating cancer cells are glioblastoma cells.

5. The aptamer of claim 1, wherein the nucleic acid is DNA.

6. The aptamer of claim 1, wherein the nucleic acid is complexed or linked to an imaging agent or an anticancer agent.

7. The aptamer of claim 1, wherein the aptamer comprises a sequence selected from the group consisting of SEQ ID NOS. 1-3 or an analog thereof.

8. A method of imaging tumor initiating cancer cells in a subject, comprising administering an effective amount of an aptamer consisting of a single stranded nucleic acid having 100 nucleotides or less and comprising a sequence selected from the group consisting of SEQ ID NOS. 1-9 or an analog thereof that specifically binds to tumor initiating cancer cells, the aptamer being complexed or linked to an imaging agent, to the subject and detecting the aptamers with an imaging apparatus.

9. The method of claim 8, wherein the aptamer is detected in vivo.

10. The method of claim 8, wherein the aptamer is detected ex vivo.

11. The method of claim 8, wherein the aptamer specifically binds to tumor initiating brain cancer cells.

12. The method of claim 8, wherein the aptamer specifically binds to tumor initiating glioblastoma cells.

13. The method of claim 8, wherein the aptamer comprises a sequence selected from the group consisting of SEQ ID NOS. 1-9, or analog thereof.

14. The method of claim 8, wherein the aptamer comprises a sequence selected from the group consisting of SEQ ID NOS. 1-3, or analog thereof.

15. A method of treating brain cancer in a subject, comprising administering an effective amount of an aptamer consisting of a single stranded nucleic acid having 100 nucleotides or less and comprising a sequence selected from the group consisting of SEQ ID NOS. 1-9 or an analog thereof that specifically binds to brain cancer cells, the aptamer being complexed or linked to an anticancer agent, to the subject.

16. The method of claim 15, wherein the brain cancer is glioblastoma and the aptamer specifically binds to glioblastoma cells.

17. The method of claim 15, wherein the aptamer specifically binds to brain tumor initiating cells.

18. The method of claim 15, wherein the aptamer comprises a sequence selected from the group consisting of SEQ ID NOS. 1-9, or analog thereof.

19. The method of claim 15, wherein the aptamer comprises a sequence selected from the group consisting of SEQ ID NOS. 1-3, or analog thereof.

20. The aptamer of claim 1, wherein the aptamer comprises SEQ ID NO. 1 or an analog thereof.

21. The aptamer of claim 1, wherein the aptamer comprises SEQ ID NO. 2 or an analog thereof.

22. The aptamer of claim 1, wherein the aptamer comprises SEQ ID NO. 3 or an analog thereof.

23. The aptamer of claim 1, wherein the aptamer comprises SEQ ID NO. 4 or an analog thereof.

24. The aptamer of claim 1, wherein the aptamer comprises SEQ ID NO. 5 or an analog thereof.

25. The aptamer of claim 1, wherein the aptamer comprises SEQ ID NO. 6 or an analog thereof.

26. The aptamer of claim 1, wherein the aptamer comprises SEQ ID NO. 7 or an analog thereof.

27. The aptamer of claim 1, wherein the aptamer comprises SEQ ID NO. 8 or an analog thereof.

28. The aptamer of claim 1, wherein the aptamer comprises SEQ ID NO. 9 or an analog thereof.

29. The aptamer of claim 1, wherein the nucleic acid has 35 nucleotides or less.

* * * * *